United States Patent [19]
Light et al.

[11] Patent Number: 4,547,594
[45] Date of Patent: Oct. 15, 1985

[54] PROCESS FOR PRODUCING SOLANONE, NORSOLANADIONE AND INTERMEDIATES THEREFOR

[75] Inventors: Kenneth K. Light, North Ogden, Utah; William L. Schreiber, Jackson; Joseph A. McGhie, Montclair, both of N.J.; Ronald P. Schreck, Old Bridge; Takao Yoshida, West Long Branch, both of N.J.; Loren B. Schreiber, Aberdeen; Ranya Muralidhara, Fair Haven, both of N.J.

[73] Assignee: International Flavors & Fragrances Inc., New York, N.Y.

[21] Appl. No.: 636,283

[22] Filed: Jul. 31, 1984

Related U.S. Application Data

[62] Division of Ser. No. 511,944, Jul. 8, 1983, Pat. No. 4,489,009, which is a division of Ser. No. 357,158, Mar. 11, 1982, Pat. No. 4,412,083.

[51] Int. Cl.$^4$ ............................................. C07C 45/63
[52] U.S. Cl. .................................. 568/392; 564/279; 568/403; 260/465.9
[58] Field of Search ................ 568/403, 392; 564/279; 260/465.9

[56] References Cited

U.S. PATENT DOCUMENTS 3,422,142  1/1969  Zuech ................................. 564/279
3,729,519  4/1973  Brossi et al. ....................... 568/417

OTHER PUBLICATIONS

Chem. Abst., vol. 82, #108, 821n (1975).
Van Leusen et al., Syn. Comm., vol. 8, p. 397–398, (1978).
Hall et al., Chem. Comm., pp. 1242–1244, (1971).

Primary Examiner—James H. Reamer
Attorney, Agent, or Firm—Arthur L. Liberman

[57] ABSTRACT

Described is a process for preparing solanone and norsolanadione wherein in preparing solanone, the compound having the structure:

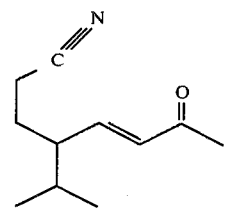

or a mixture of compounds defined according to the structure:

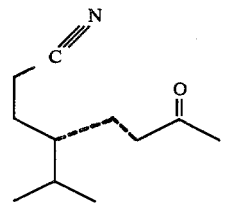

is reacted with methyl lithium and the resulting intermediate is hydrolyzed and the resulting compound is dehydrated and wherein in preparing norsolanadione this compound or mixture of compounds is reacted with ethylene glycol or propylene glycol thereby forming a ketal and the resulting ketal is reacted with methyl lithium and the resulting intermediate is then hydrolyzed in the presence of acid in which one of the dashed lines represents a carbon-carbon single bond and the other of the dashed lines represents a carbon-carbon double bond.

1 Claim, 27 Drawing Figures

GLC PROFILE FOR EXAMPLE II.

GLC PROFILE FOR EXAMPLE II.

GLC PROFILE FOR EXAMPLE II. CRUDE

GLC PROFILE FOR FRACTION 2 OF EXAMPLE II.

GLC PROFILE FOR BULKED FRACTIONS 4-11 OF EXAMPLE II.

GLC PROFILE FOR EXAMPLE III. CRUDE

GLC PROFILE FOR BULKED FRACTIONS 1-4 OF EXAMPLE III.

GLC PROFILE FOR EXAMPLE V. CRUDE

GLC PROFILE FOR EXAMPLE V. DISTILLATION PRODUCT

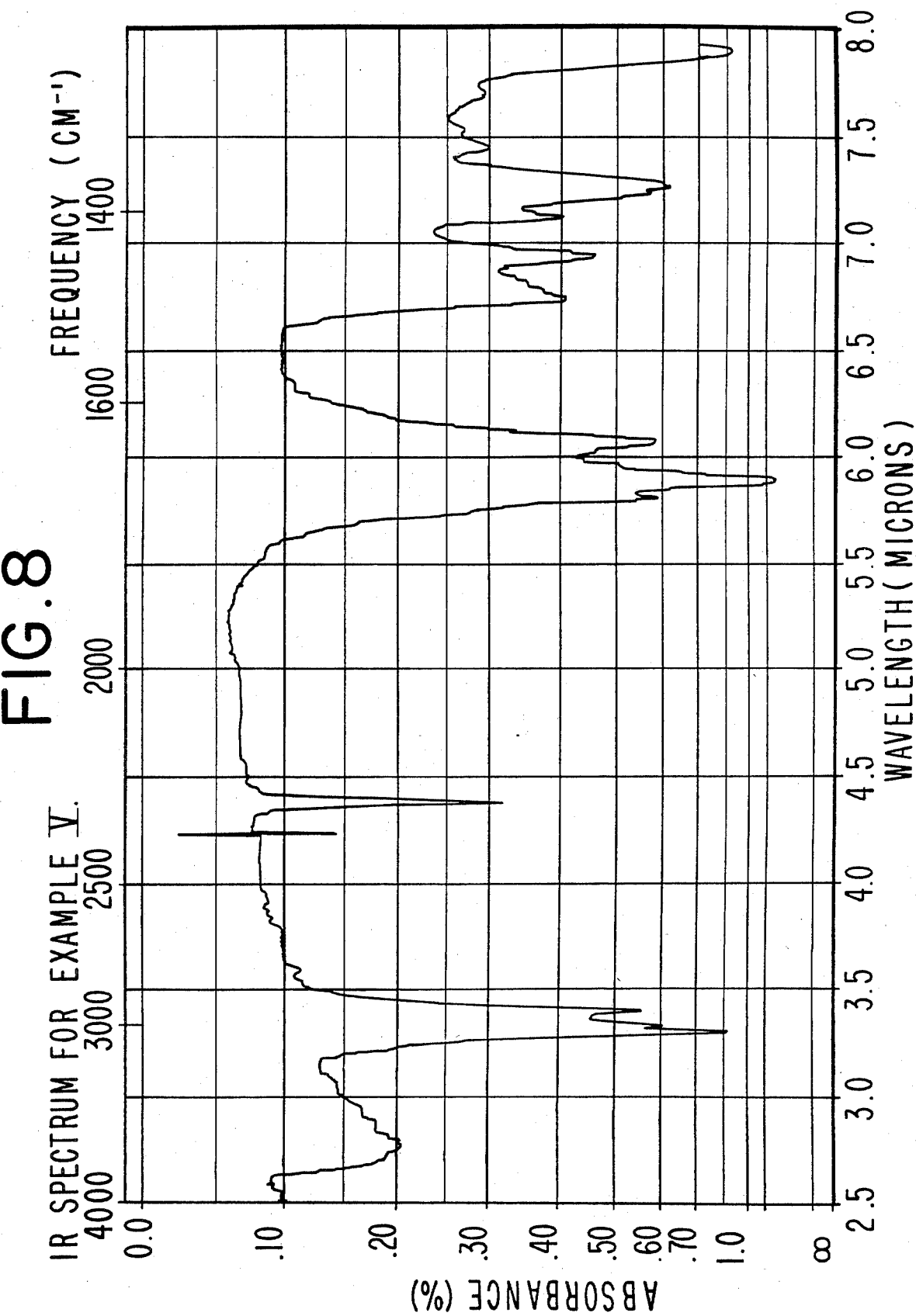

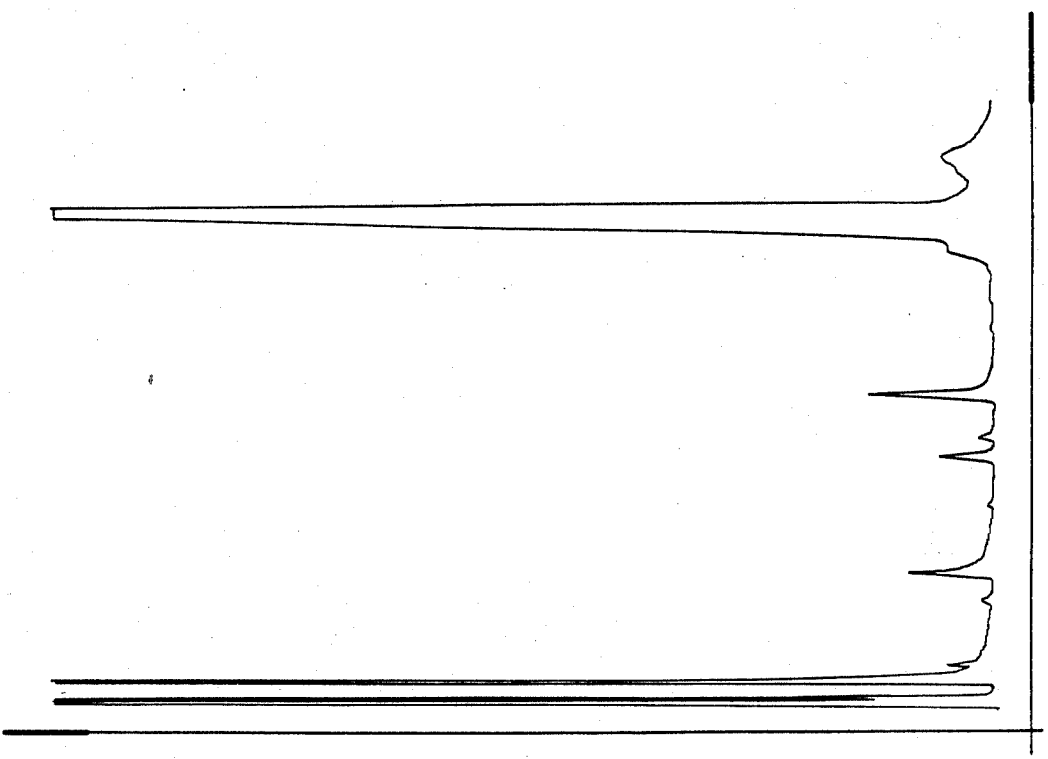
FIG. IO
GLC PROFILE FOR EXAMPLE VII.
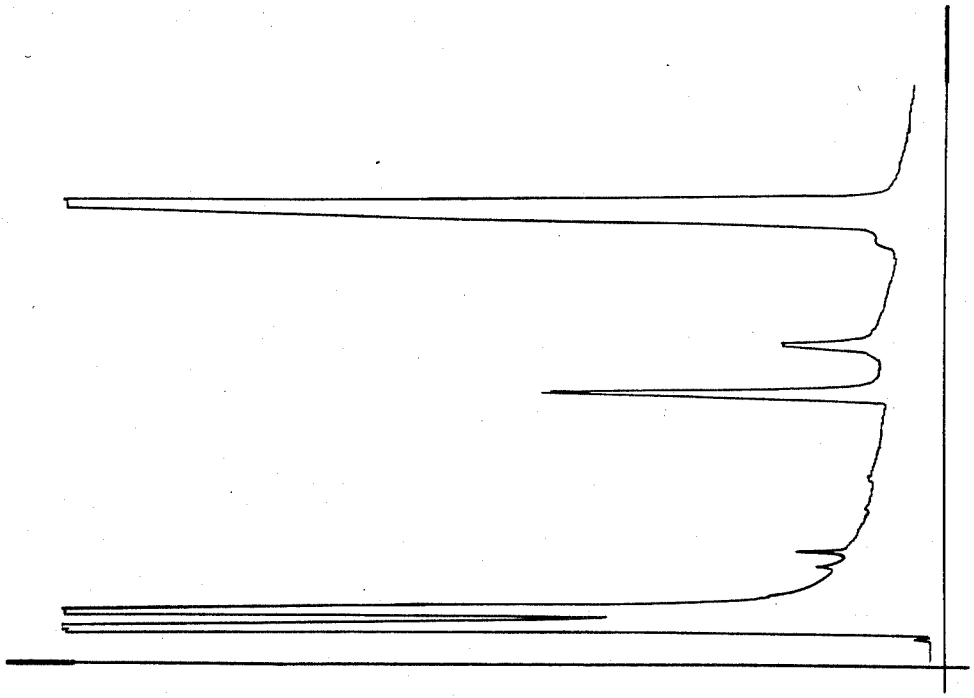
FIG. 9
GLC PROFILE FOR EXAMPLE VI.
CRUDE

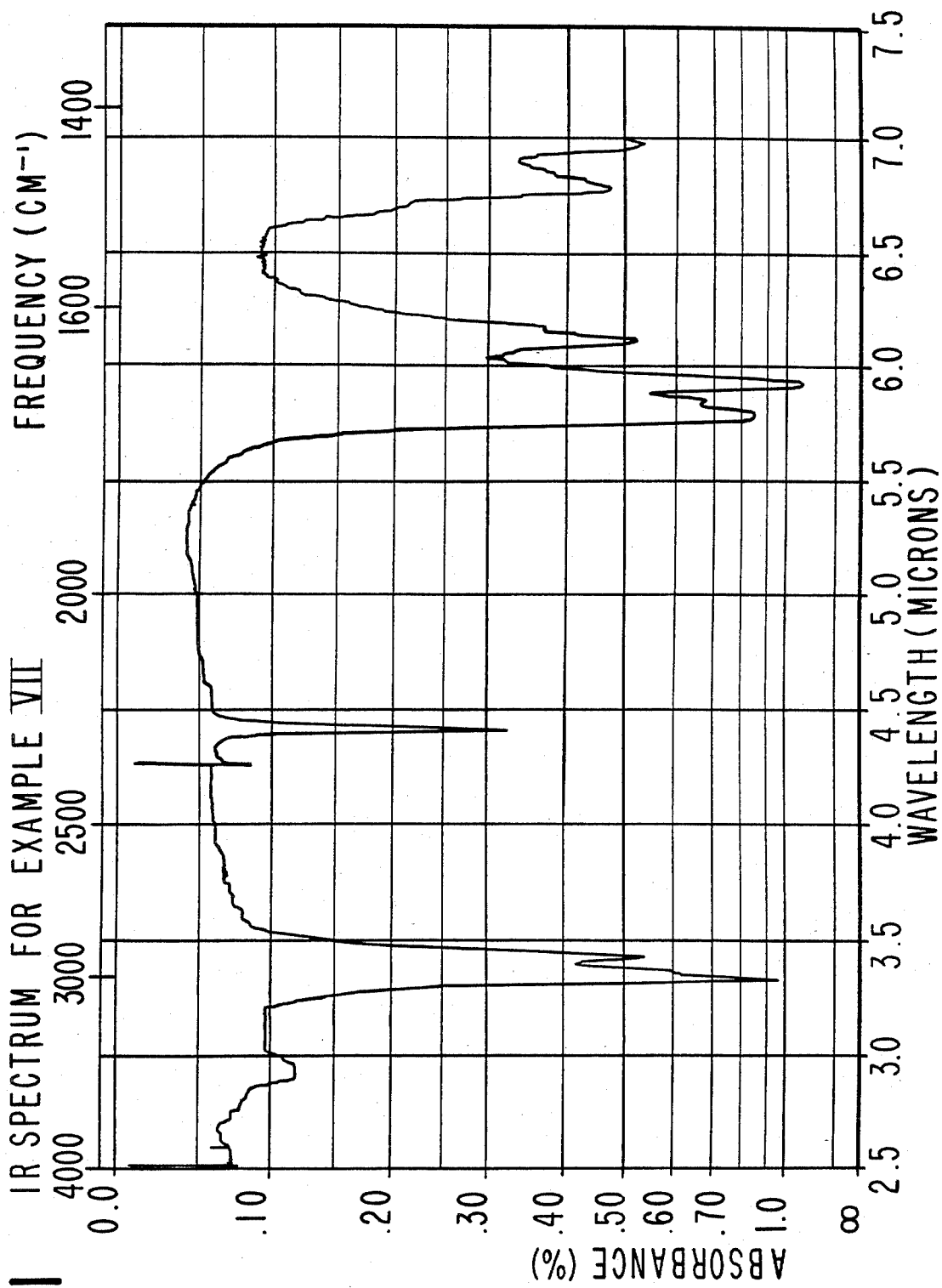
FIG.11 IR SPECTRUM FOR EXAMPLE VII

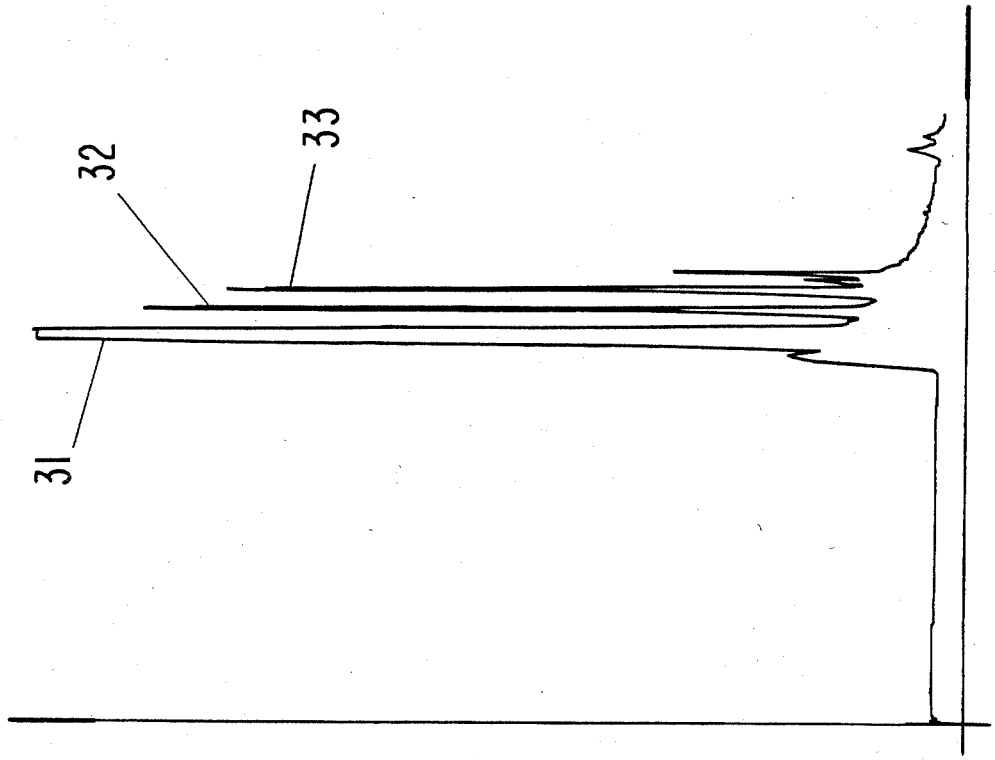
FIG.14 GLC PROFILE FOR EXAMPLE IX. BULKED FRACTIONS 6-10
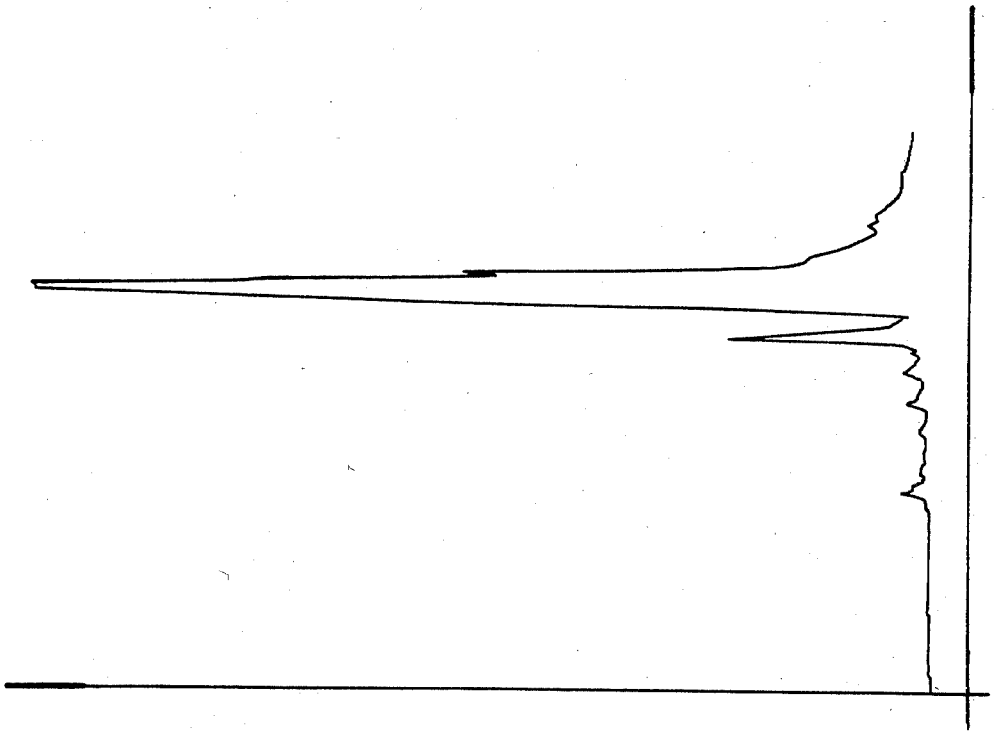
FIG.12 GLC PROFILE FOR EXAMPLE VIII. CRUDE

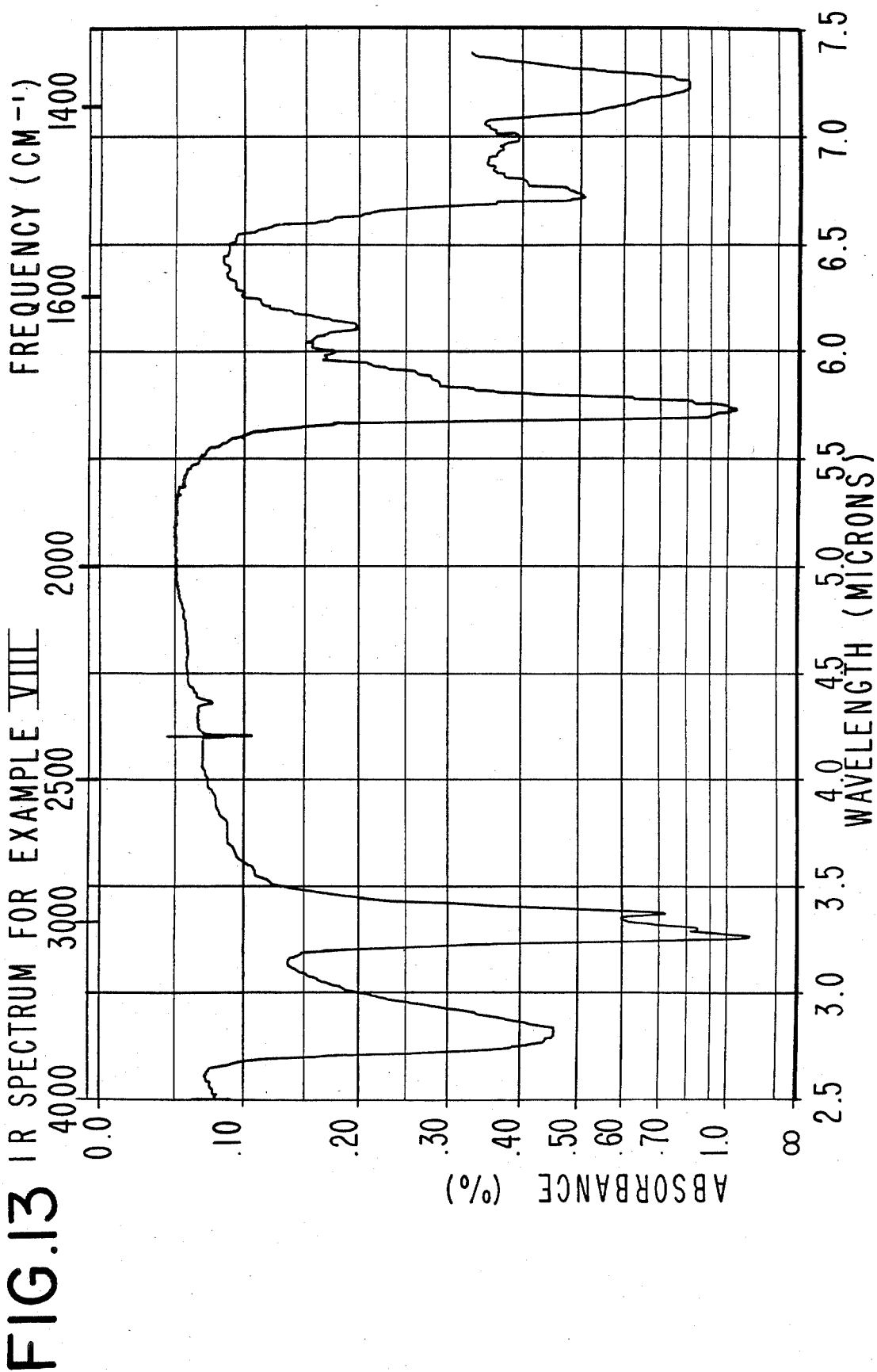
FIG.13 IR SPECTRUM FOR EXAMPLE VIII

GLC PROFILE FOR EXAMPLE X.

FIG.16 NMR SPECTRUM FOR PEAK 41 OF FIG.15 OF EXAMPLE X.

IR SPECTRUM FOR EXAMPLE XII

MASS SPECTRUM FOR FRACTION 3 OF EXAMPLE XII.

GLC PROFILE FOR EXAMPLE XIV.

GLC PROFILE FOR EXAMPLE XIII.

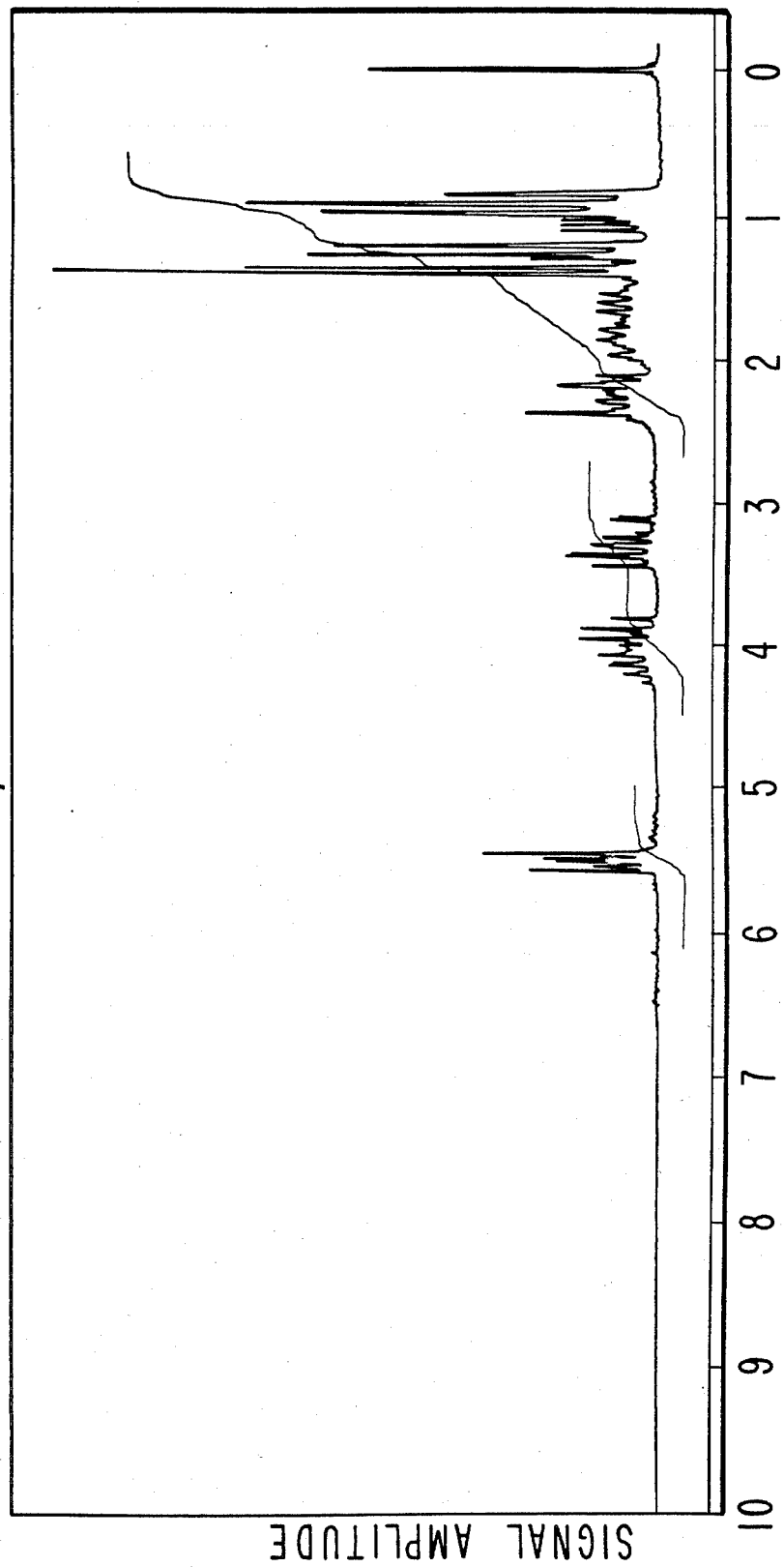

IR SPECTRUM FOR FRACTION 5 OF EXAMPLE XIV

GLC PROFILE FOR EXAMPLE XV.
CRUDE

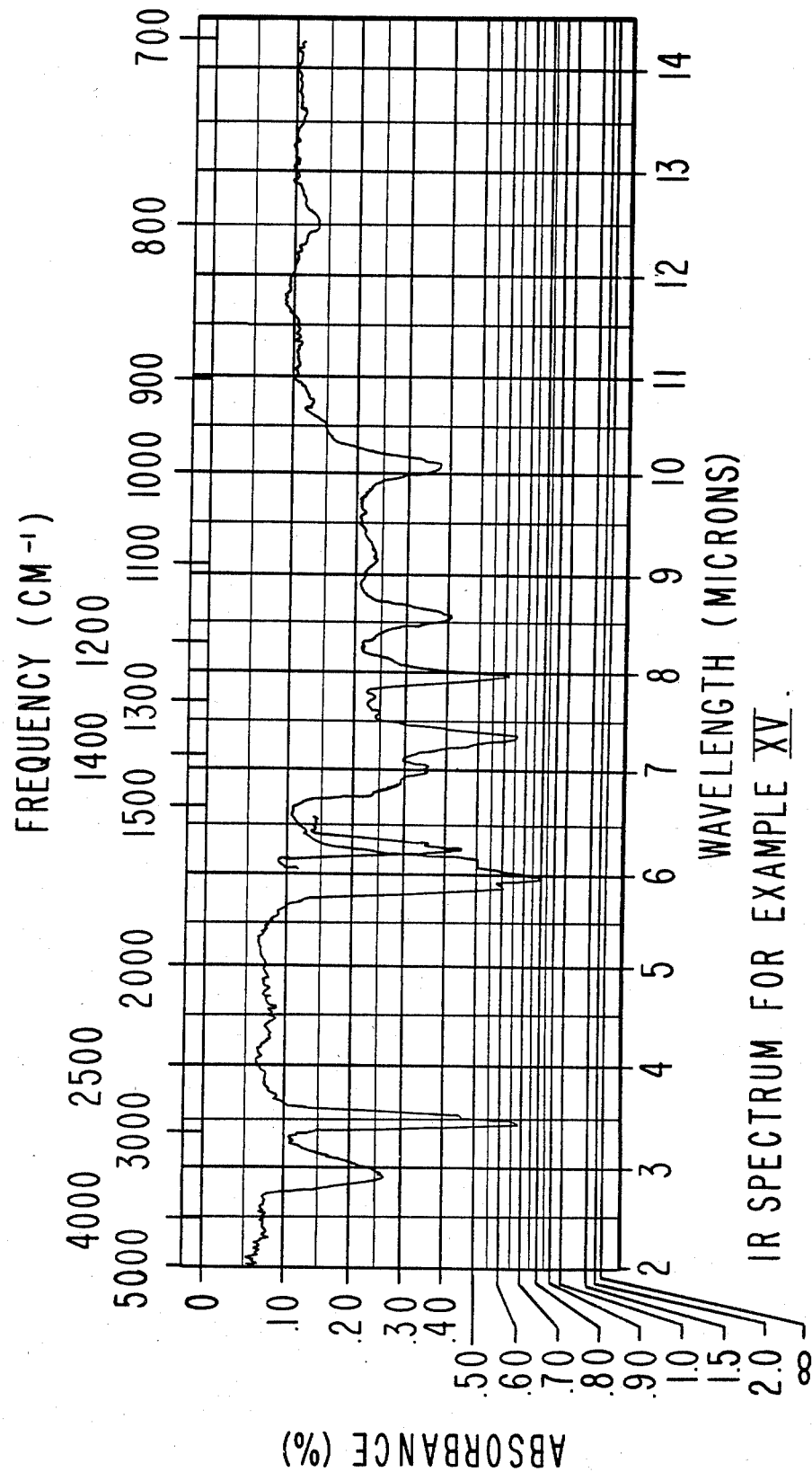

PROCESS FOR PRODUCING SOLANONE, NORSOLANADIONE AND INTERMEDIATES THEREFOR

This is a divisional of application Ser. No. 511,944, filed 7/8/83, now U.S. Pat. No. 4,489,009, which, in turn, is a divisional of application for U.S. Letters Patent, Ser. No. 357,158 filed on 3/11/82, now U.S. Pat. No. 4,412,083 issued 10/25/83.

BACKGROUND OF THE INVENTION

Solanone is known as a useful tobacco flavorant and flavor enhancer. It is a mixture consisting primarily of the compound:

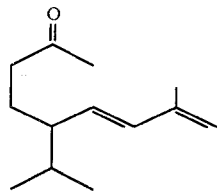

and, in addition, a small amount of the compound having the structure:

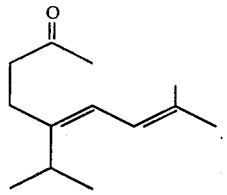

Norsolanadione is another compound known to be useful as a tobacco flavorant and in augmenting or enhancing the aroma and taste of smoking tobacco. Norsolanadione has the structure:

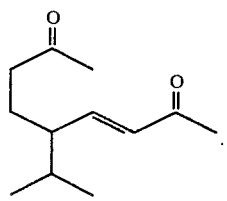

Both norsolanadione and solanone have been previously synthesized using cumbersome, economically unfeasible reactions, e.g. reactions including the Wittig or Emmons reaction.

The compound having the structure:

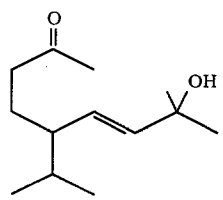

has been isolated from Burley tobacco flavor as set forth in Chem. Abstracts 1974, 35704g and in the article by Demole et al, Helv. Chim. Acta, 1974, 57(1) pages 192–4. This material known as "solanone hydrate" is also shown to be synthesized in Chem. Abstracts 85:108821n via a complex, multi-step synthesis.

The present invention provides an efficient, low cost synthesis for preparation of solanone, norsolanadione and solanone hydrate having the structure:

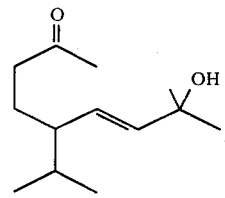

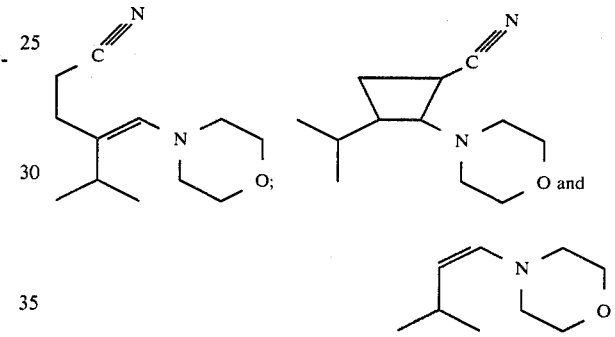

(conditions: SE-30 column programmed at 100°–220° C. at 8° C. per minute).

Figure 2:
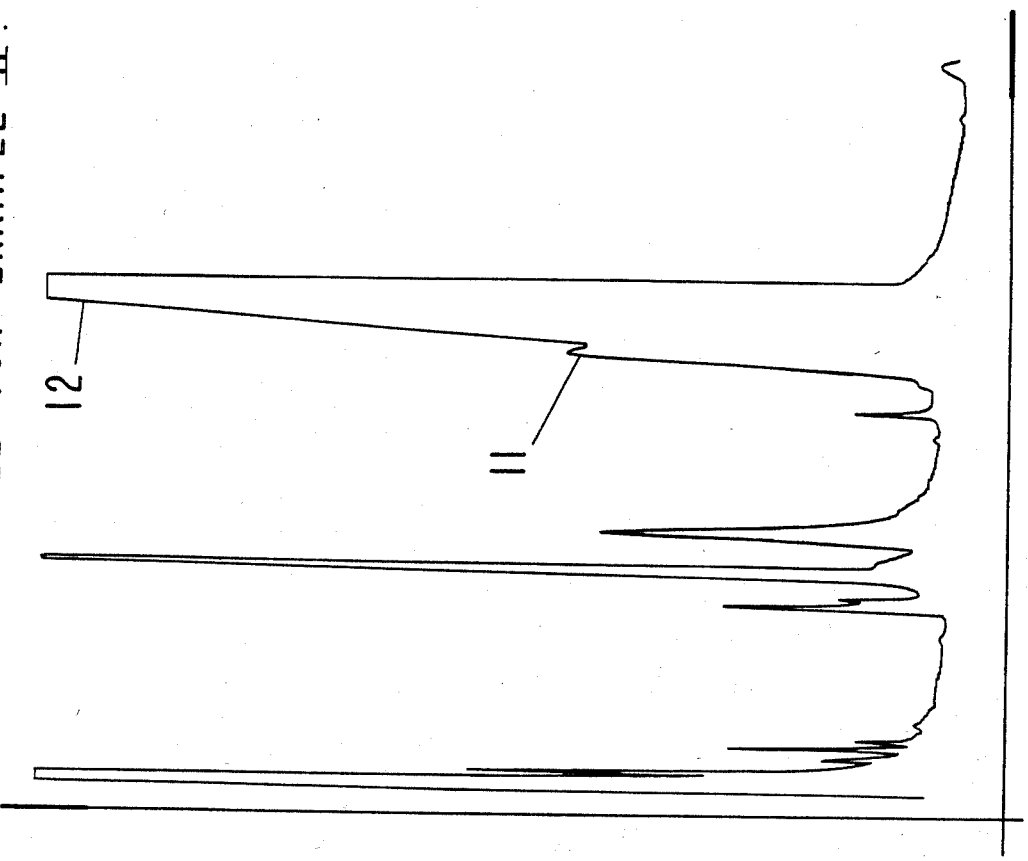

FIG. 2 is the GLC profile of the reaction product prior to hydrolysis of Example II containing the compounds having the structures:

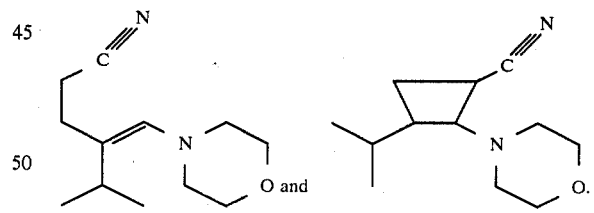

Figure 3:
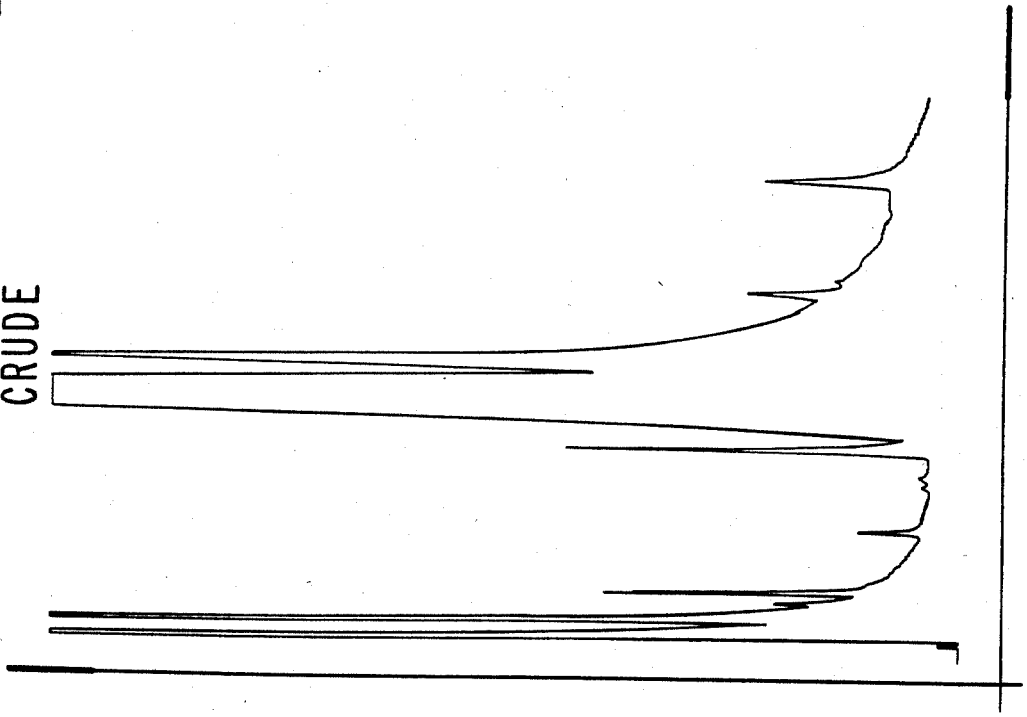

FIG. 3 is the GLC profile for the reaction product of Example II subsequent to hydrolysis (crude reaction product) having the structure:

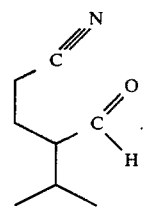

Figure 4B:
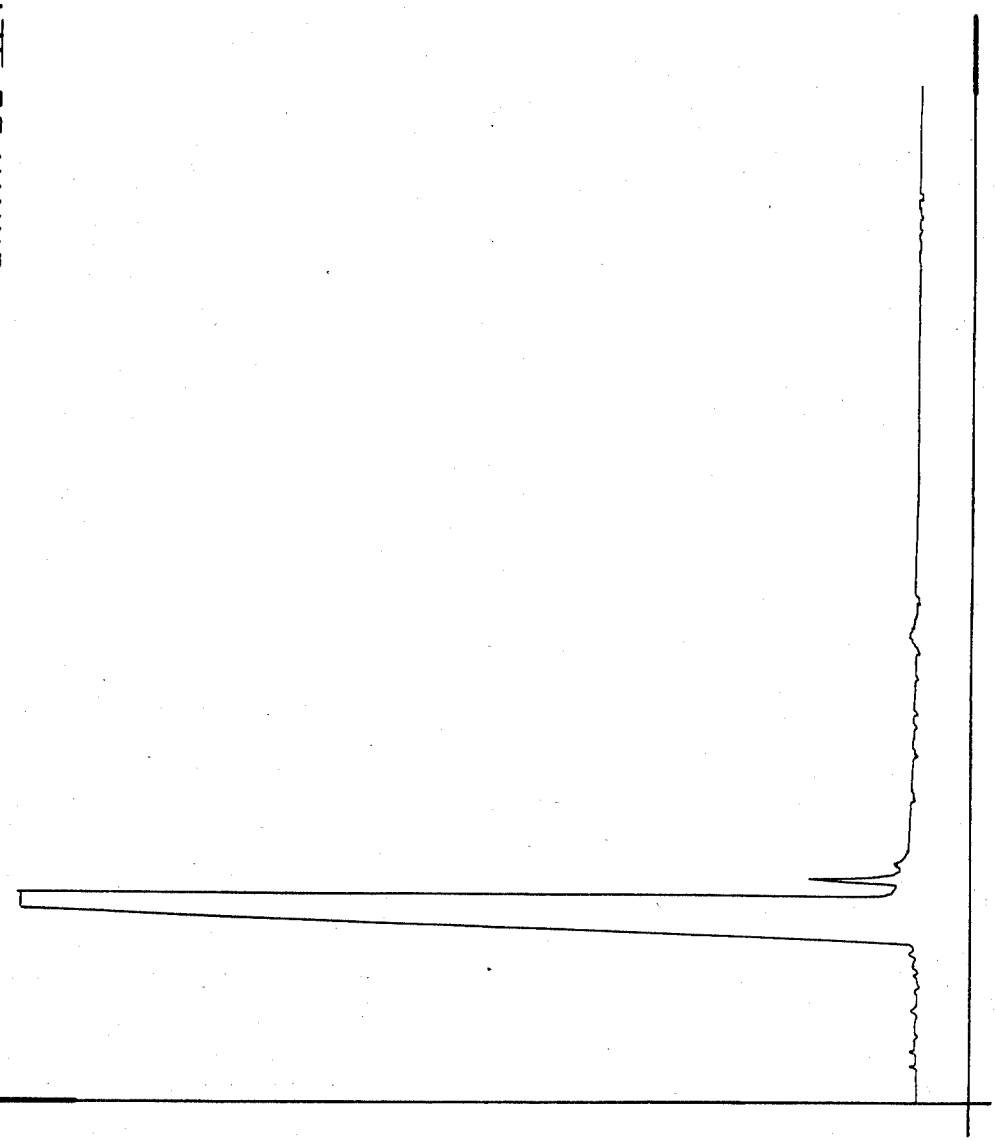
Figure 4A:
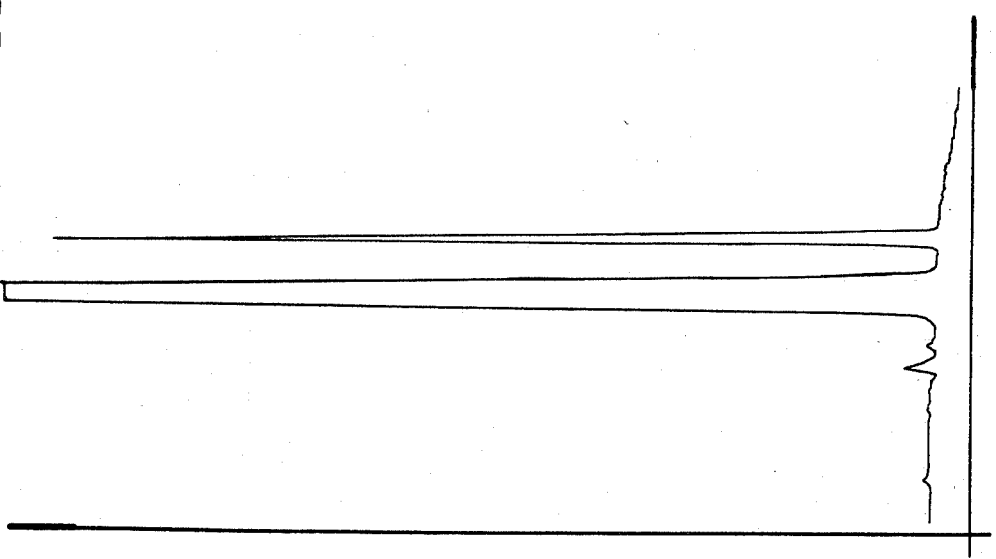

FIG. 4A is the GLC profile for bulked fractions 4–11 of the distillation product of the reaction product of Example II containing the compound having the structure:

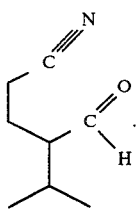

FIG. 4B is the GLC profile for fraction 2 of the distillation product of the reaction product of Example II containing the compound having the structure:

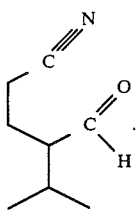

Figure 5:
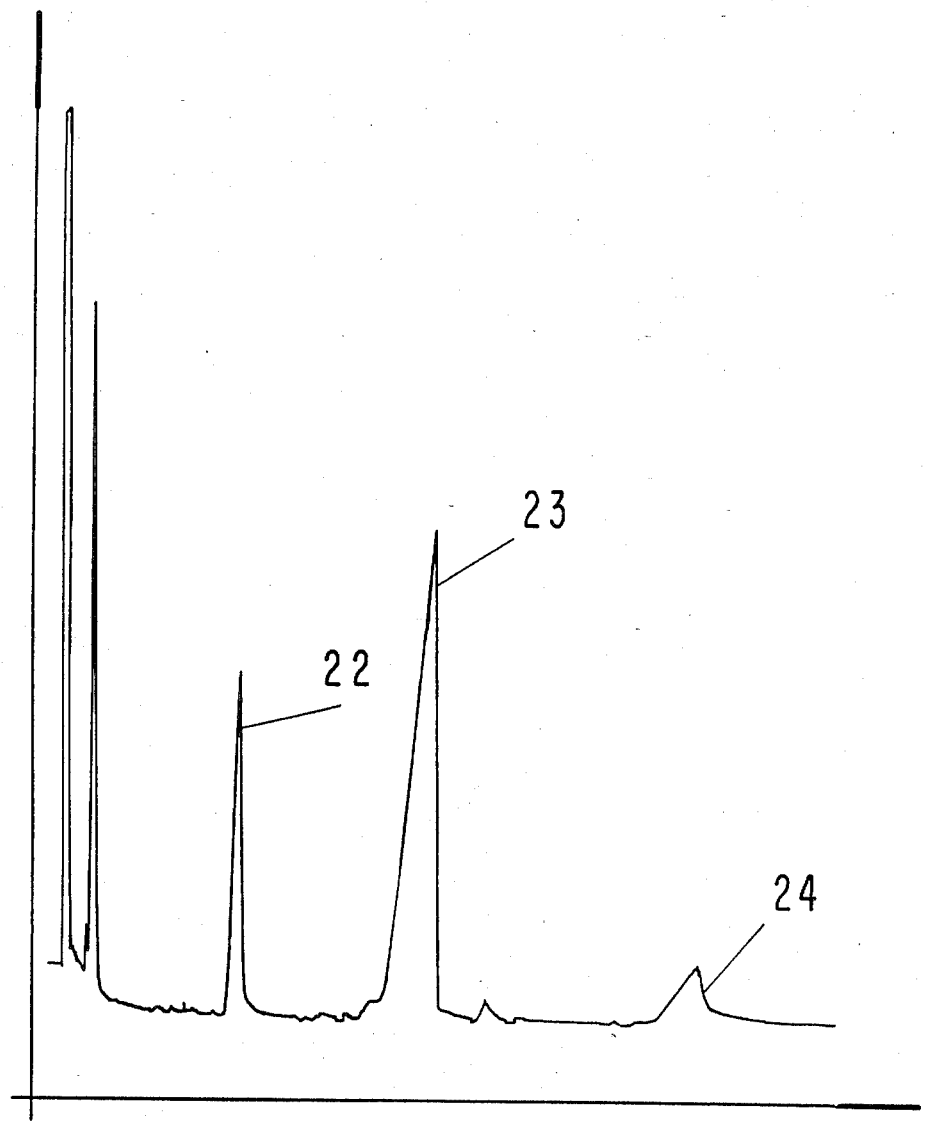

FIG. 5 is the GLC profile for the crude reaction product of Example III containing the compounds having the structures:

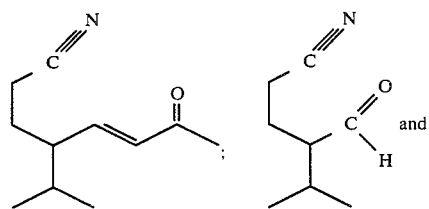

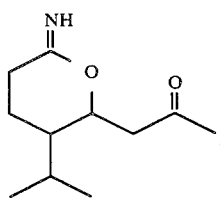

Figure 6:
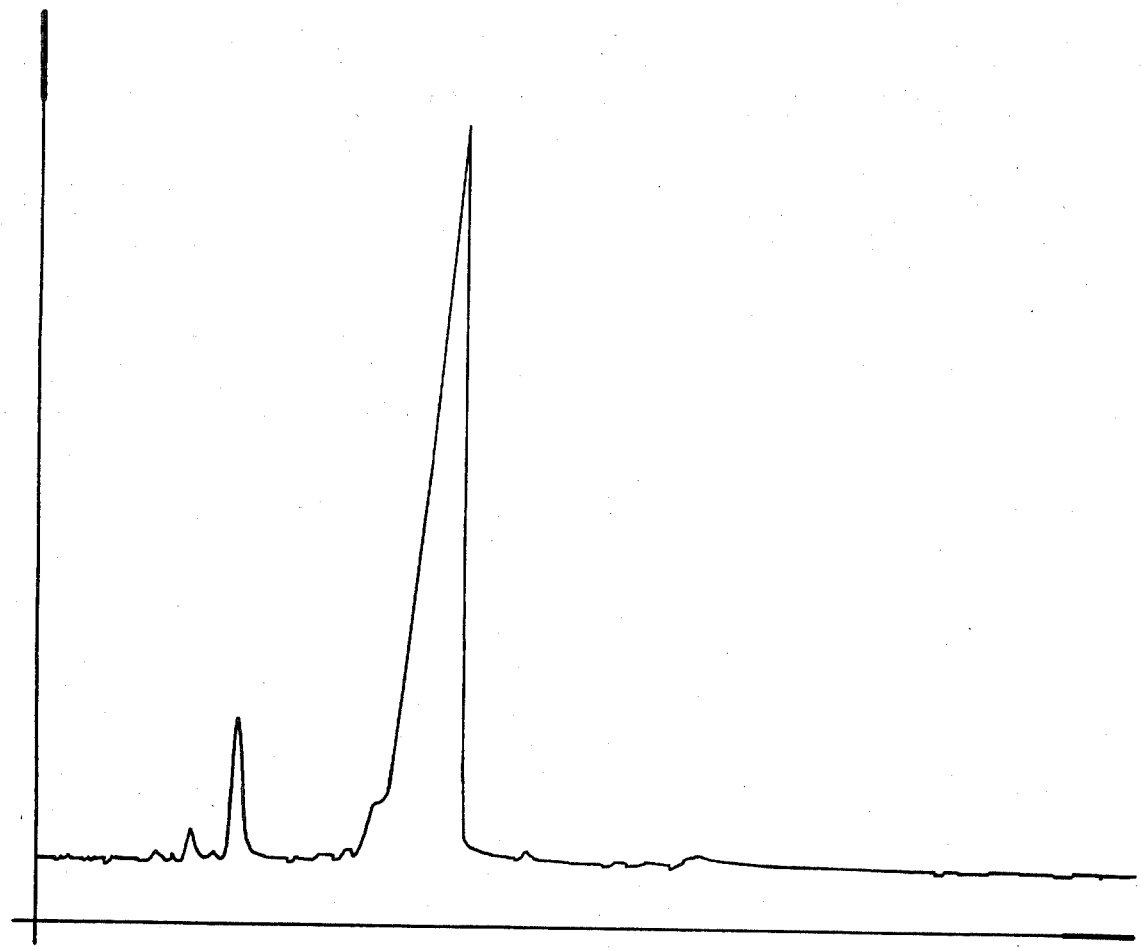

FIG. 6 is the GLC profile for bulked fractions 1–4 of the distillation product of the reaction product of Example III containing the compound having the structure:

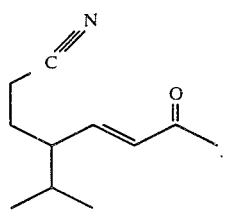

Figure 7A:
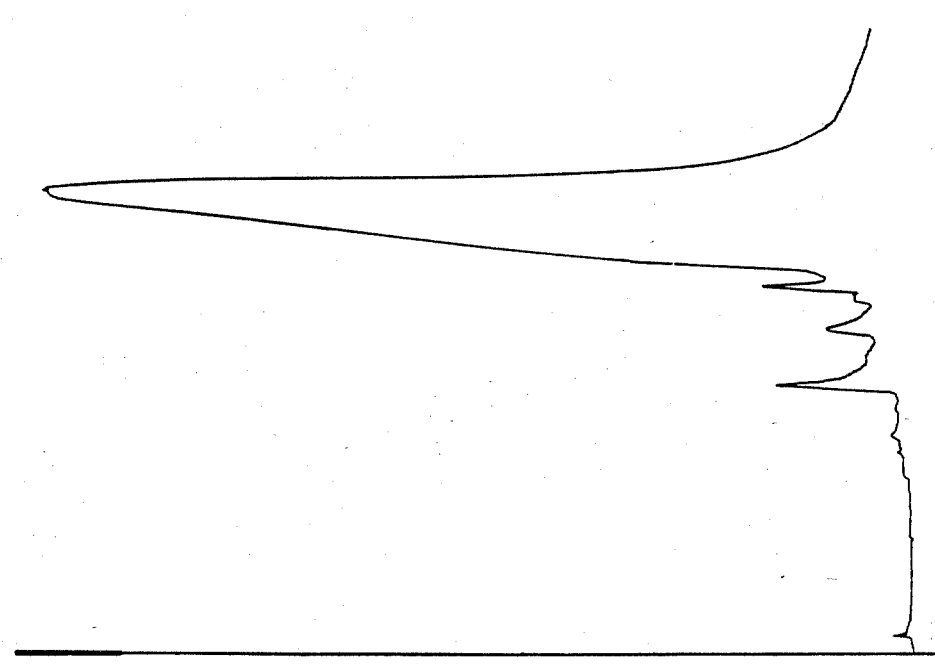

FIG. 7A is the GLC profile for the crude reaction product of Example V containing the compound having the structure:

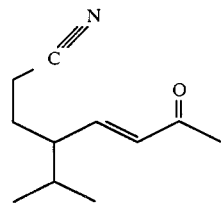

Figure 7B:
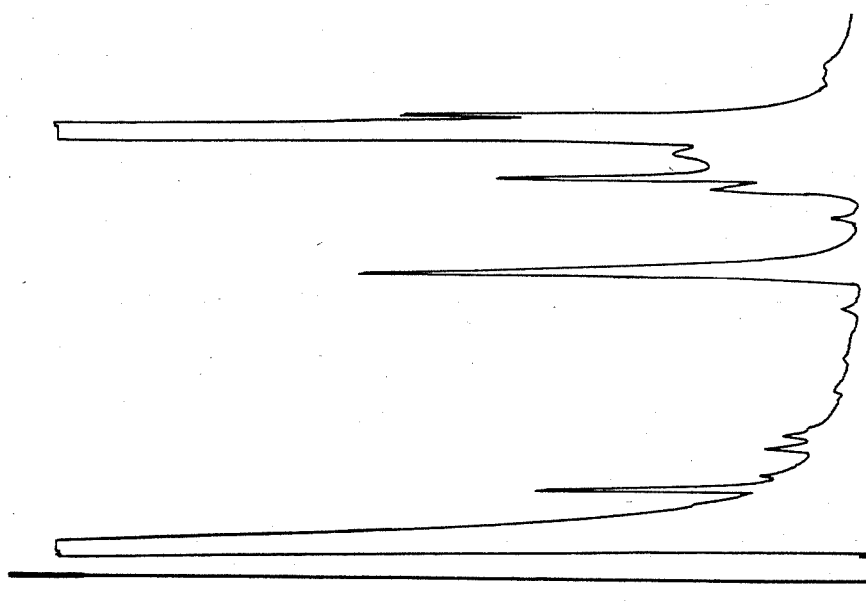

FIG. 7B is the GLC profile for the distillation product of the reaction product of Example V containing the compound having the structure:

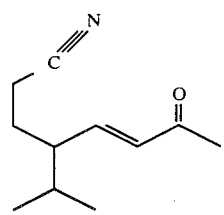

(conditions: SE-30 column programmed at 100°–220° C. at 8° C. per minute).

FIG. 8 is the infra-red spectrum for the compound produced according to Example V having the structure:

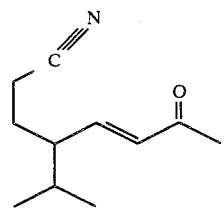

FIG. 9 is the GLC profile for the crude reaction product of Example VI containing the compound having the structure:

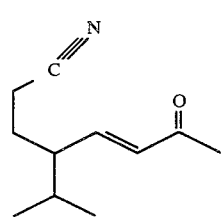

FIG. 10 is the GLC profile for the reaction product of Example VII containing the compound having the structure:

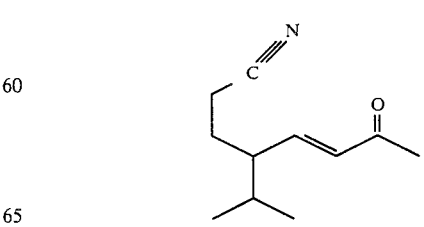

(conditions: SE-30 column programmed at 100°–220° C. at 8° C. per minute).

FIG. 11 is the infra-red spectrum for the compound having the structure:

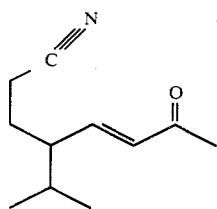

produced according to Example VII.

FIG. 12 is the GLC profile for the reaction product of Example VIII containing the compound having the structure:

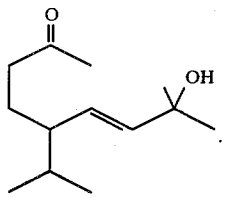

FIG. 13 is the infra-red spectrum for the compound having the structure:

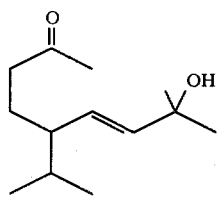

produced according to Example VIII.

FIG. 14 is the GLC profile for bulked fractions 6-10 of the distillation product of the reaction product of Example XI containing the compounds having the structures:

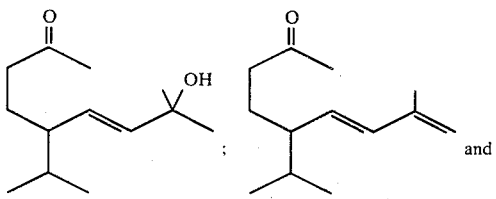

Figure 15:
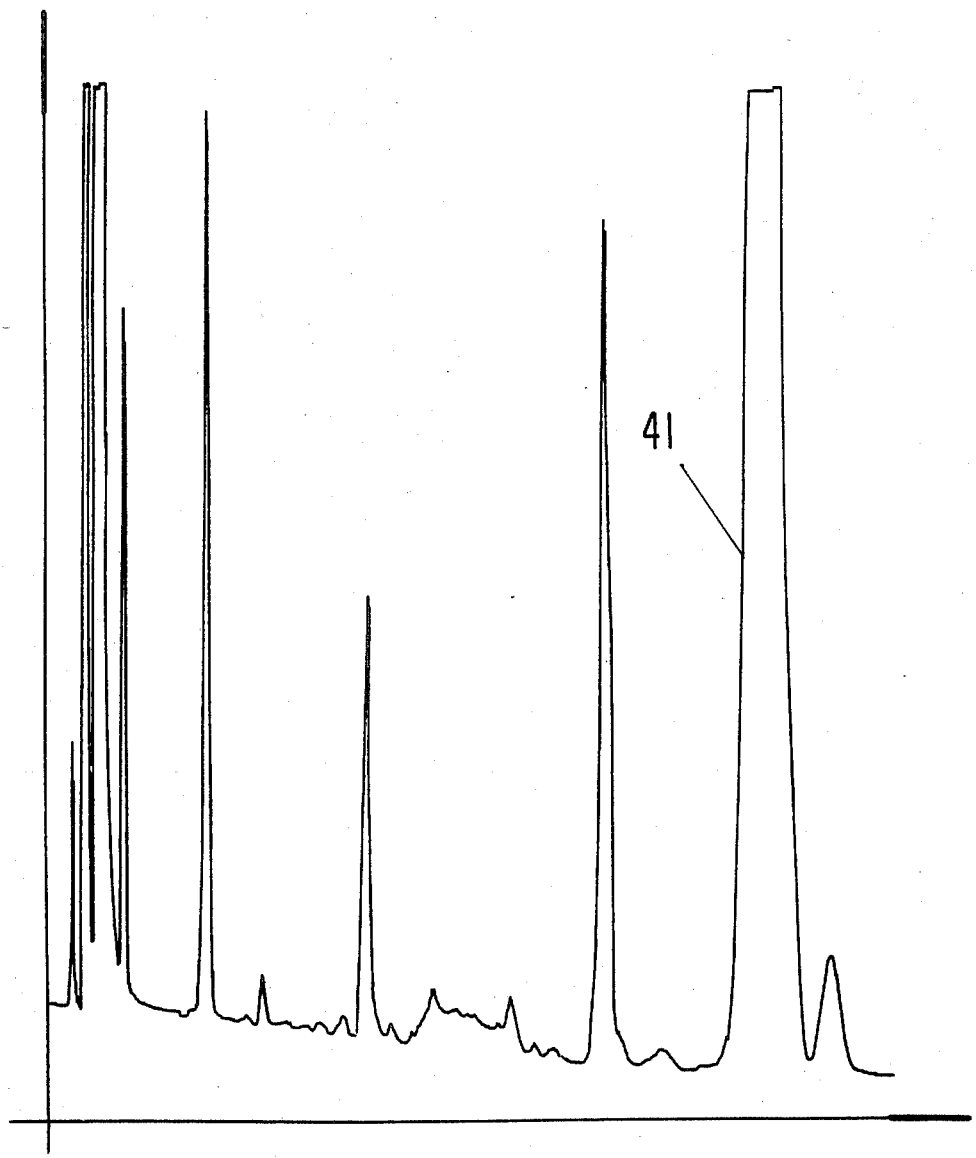

FIG. 15 is the GLC profile for the reaction product of Example X containing the compound having the structure:

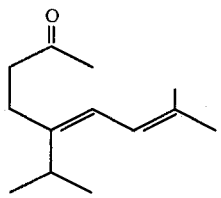

Figure 16:
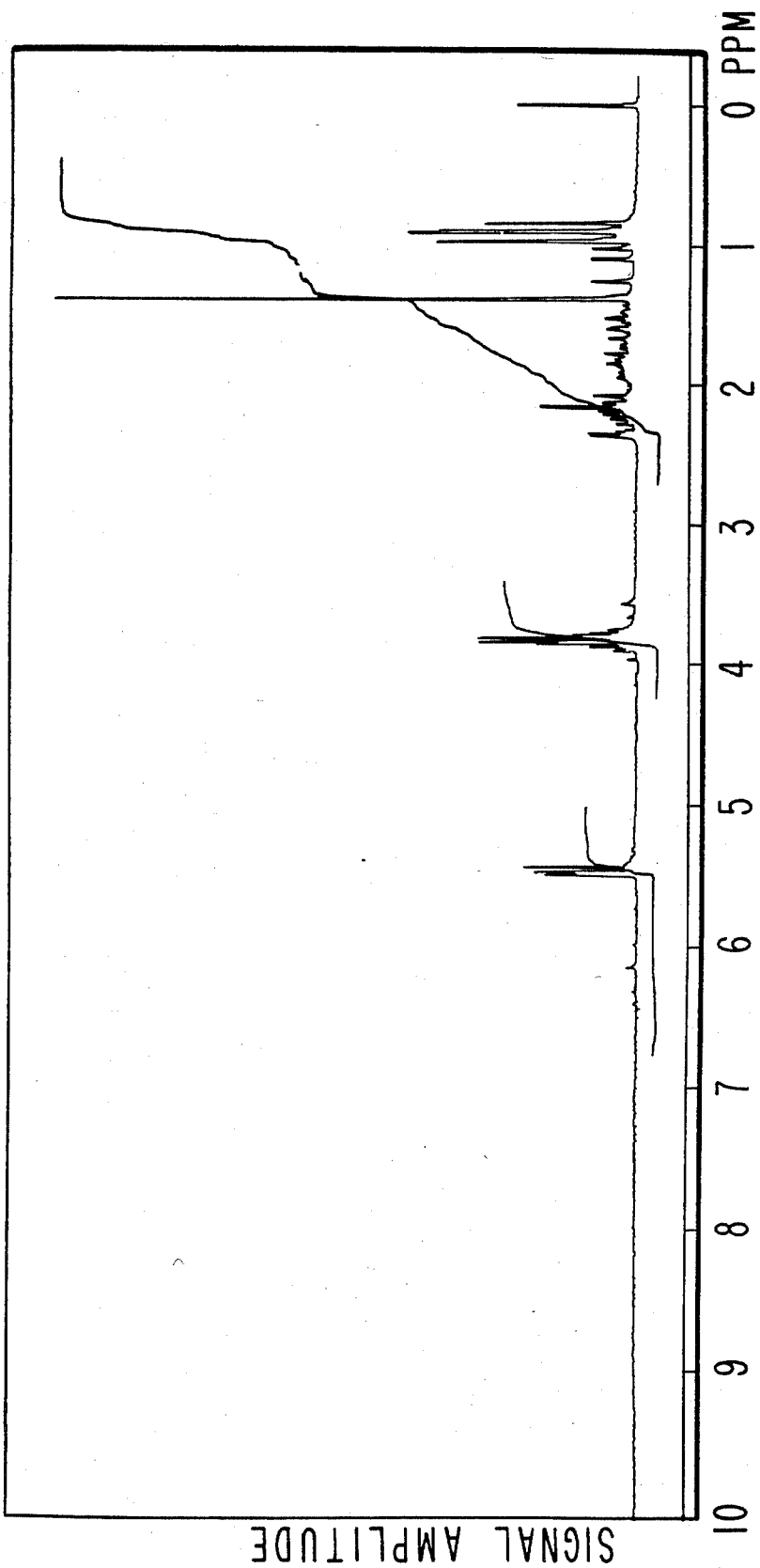

FIG. 16 is the NMR spectrum for the compound of Peak 41 of FIG. 15 for the compound having the structure:

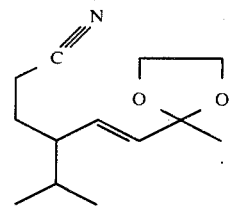

Figure 17:
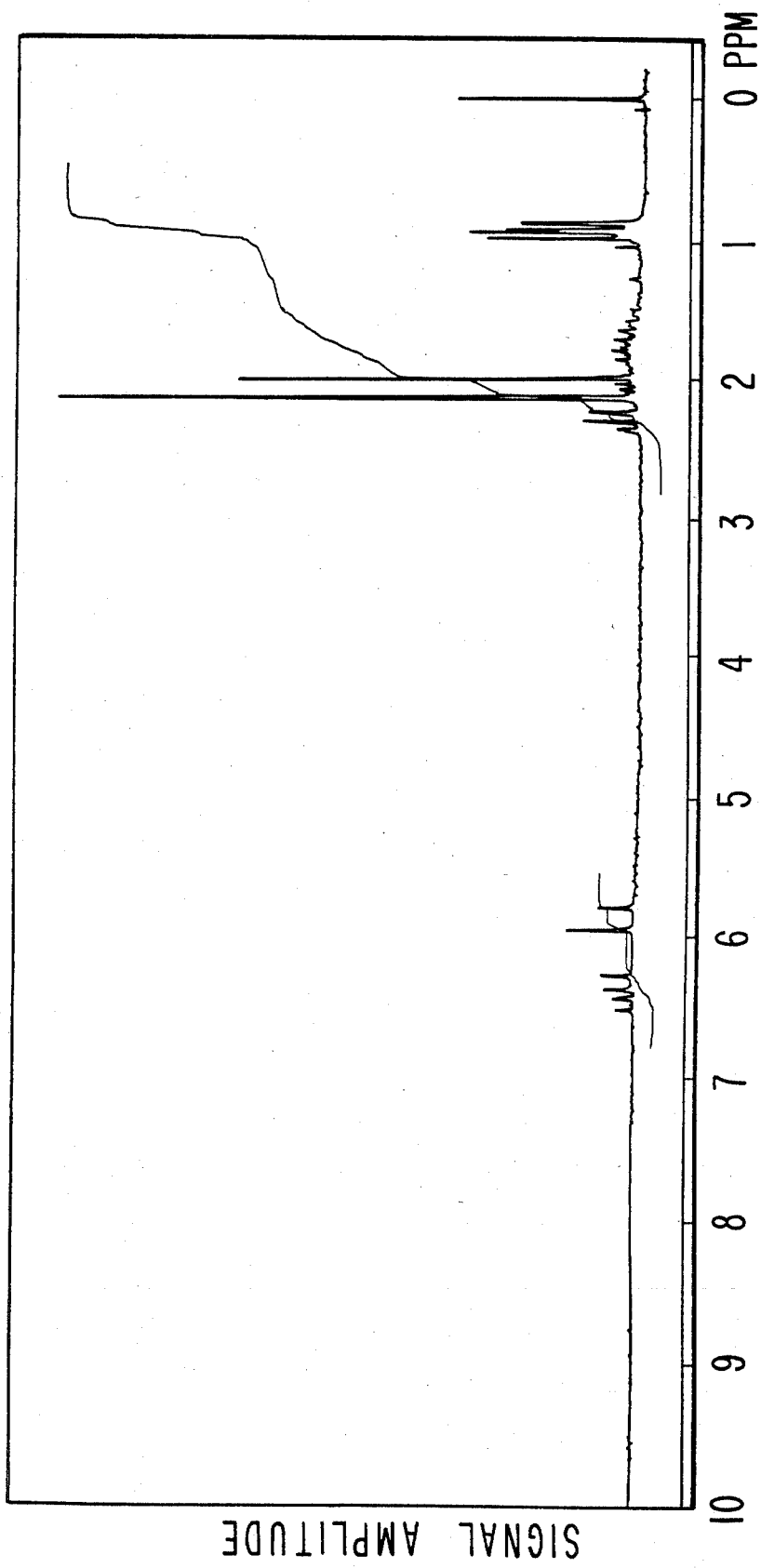

FIG. 17 is the NMR spectrum for the compound produced according to Example XI having the structure:

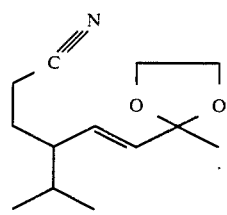

Figure 18:
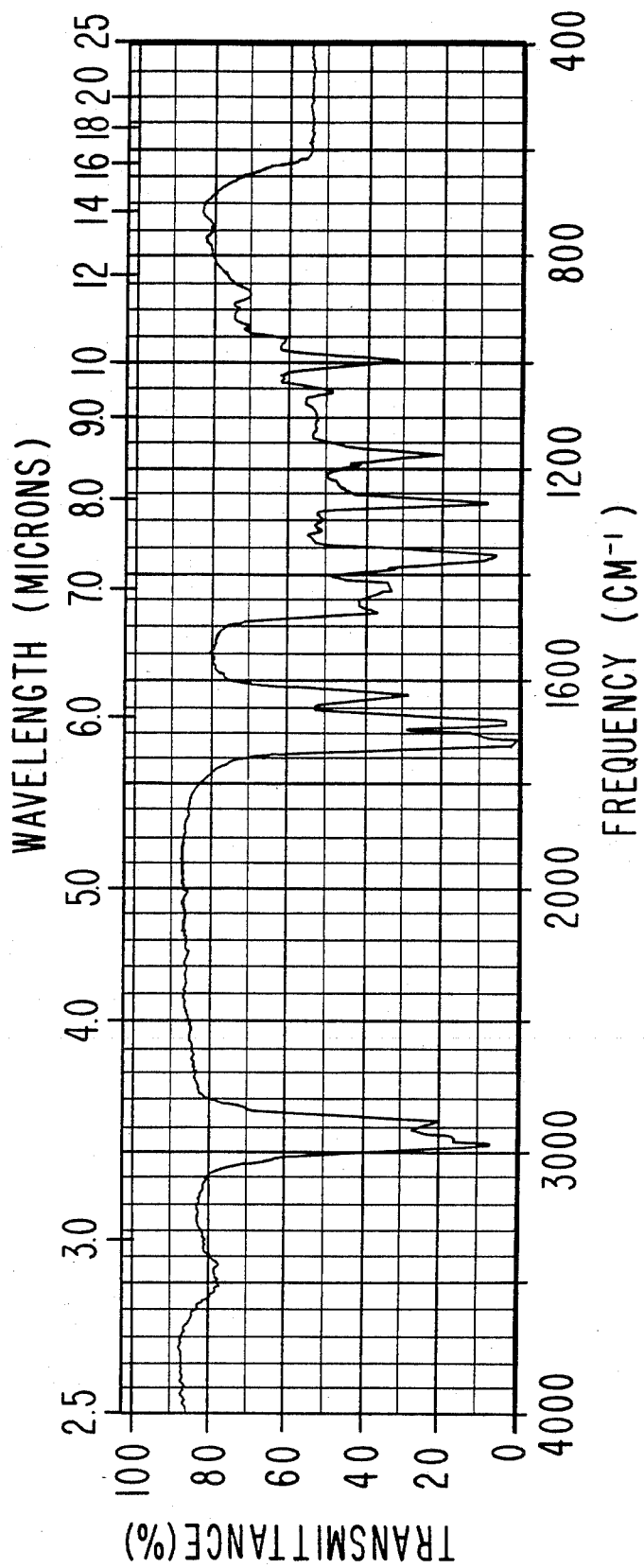

FIG. 18 is the infra-red spectrum for the reaction product of Example XII containing the compound having the structure:

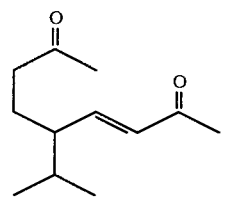

Figure 19:
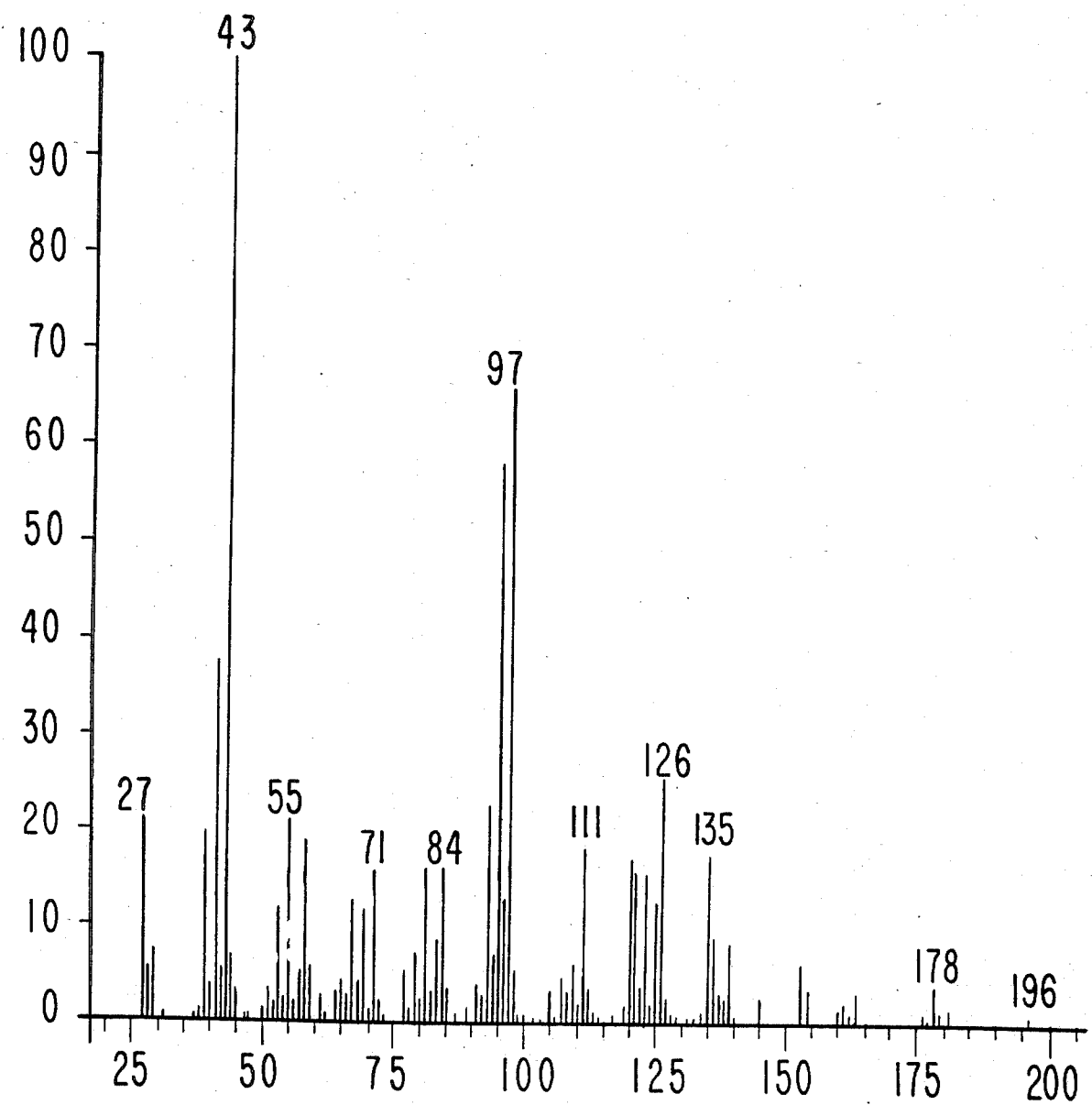

FIG. 19 is the mass spectrum for fraction 3 of the distillation product of Example XII containing the compound having the structure:

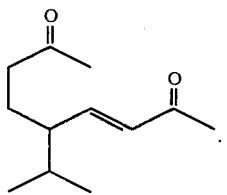

Figure 20:
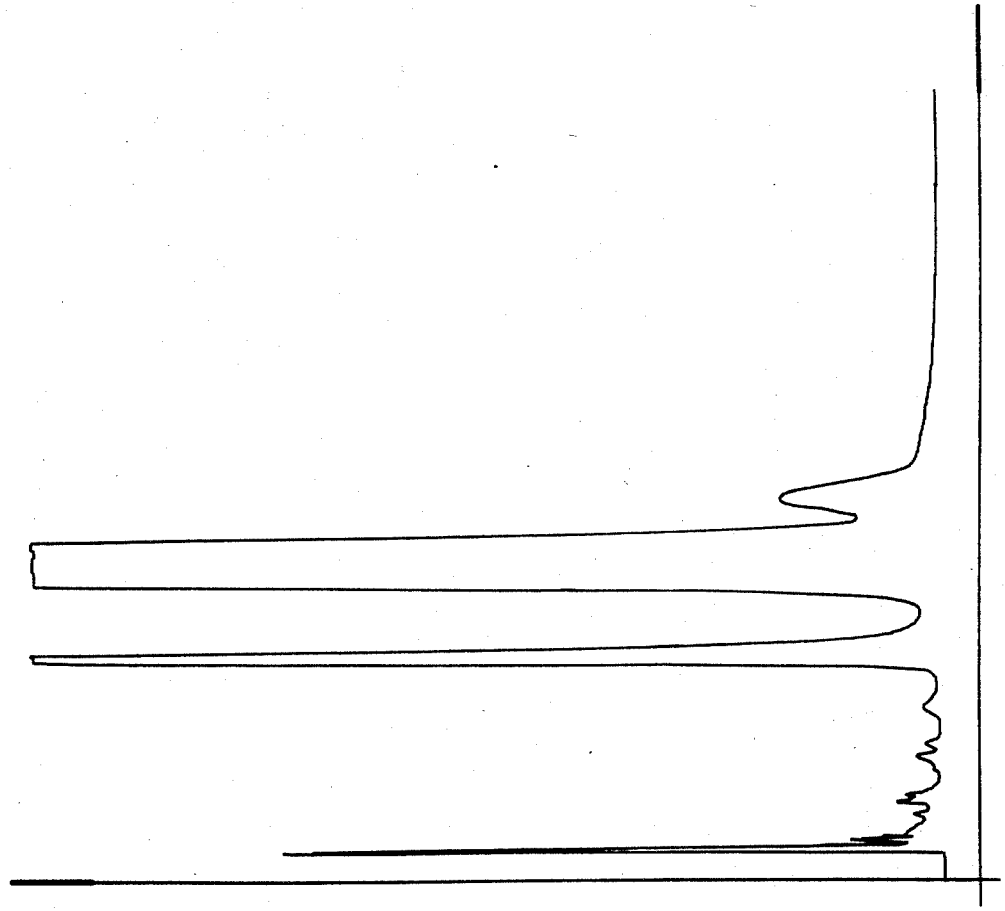

FIG. 20 is the GLC profile for the reaction product of Example XIII containing the compound having the structure:

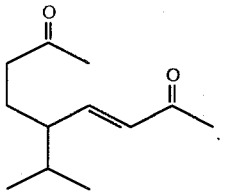

Figure 21:
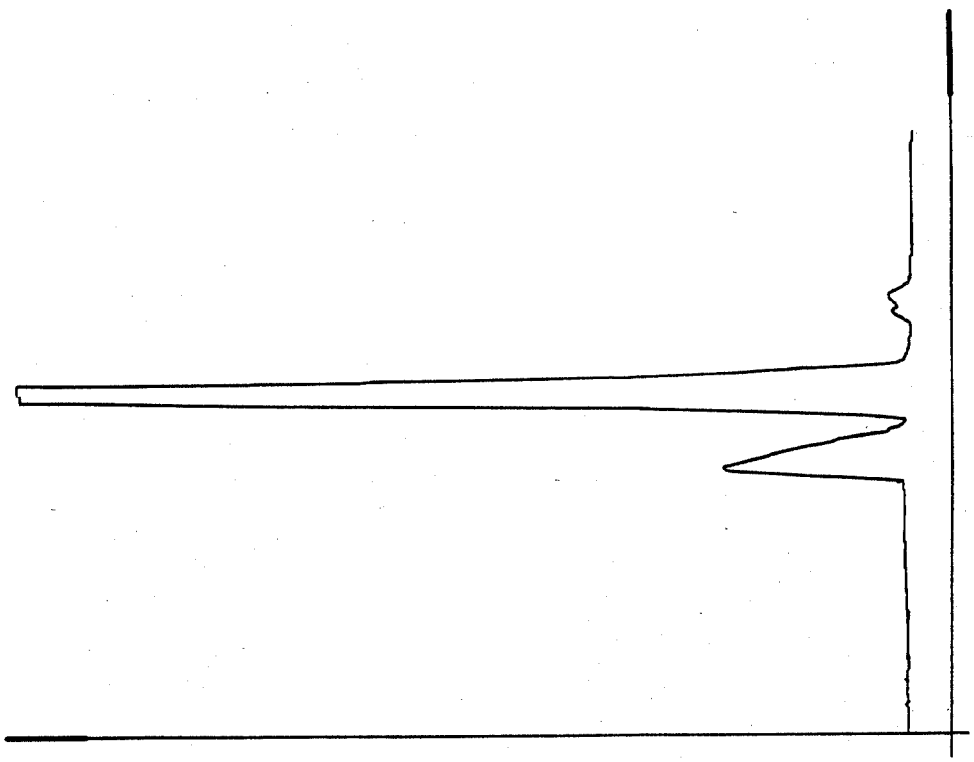

FIG. 21 is the GLC profile for the reaction product of Example XIV containing the compound having the structure:

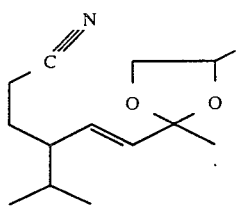

FIG. 22 is the NMR spectrum for fraction 5 of the distillation product of the reaction product of Example XIV containing the compound having the structure:

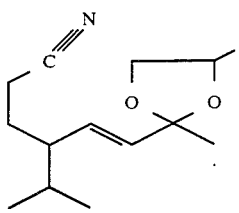

Figure 23:
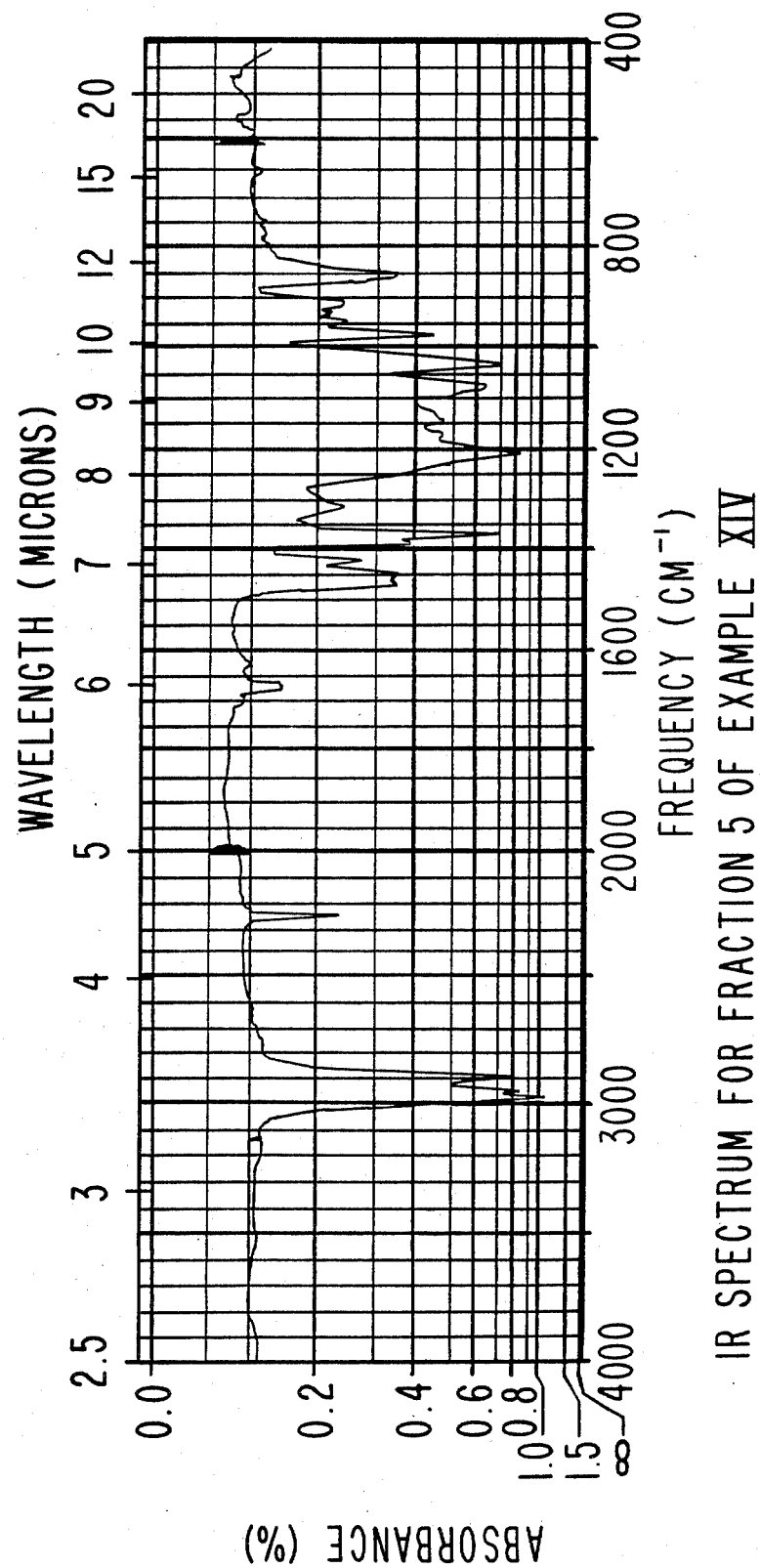

FIG. 23 is the infra-red spectrum for fraction 5 of the distillation product of the reaction product of Example XIV containing the compound having the structure:

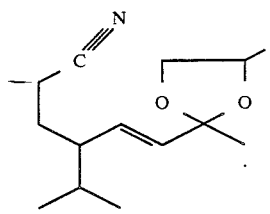

Figure 24:
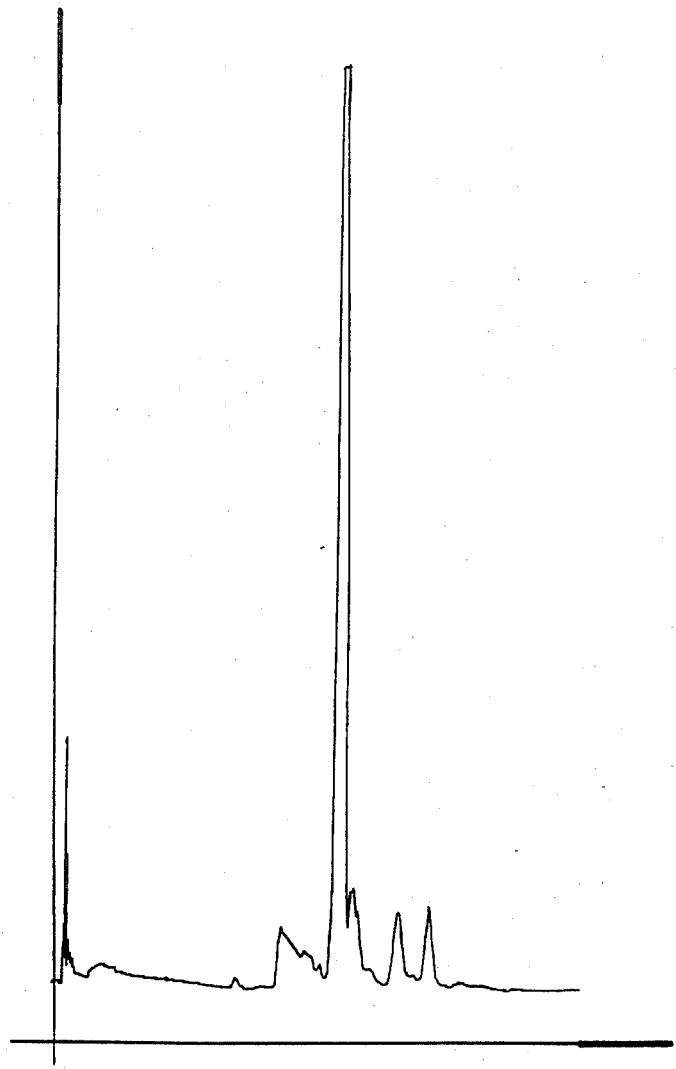

FIG. 24 is the GLC profile for the crude reaction product for Example XV containing the compound having the structure:

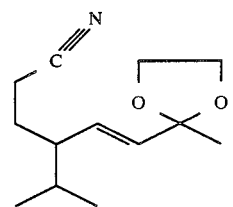

(conditions: Carbowax column programmed at 150°–220° C. at 8° C. per minute).

FIG. 25 is the infra-red spectrum for the compound having the structure:

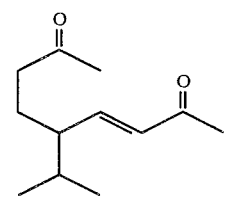

produced according to Example XV.

DETAILED DESCRIPTION OF THE DRAWINGS

Figure 1:
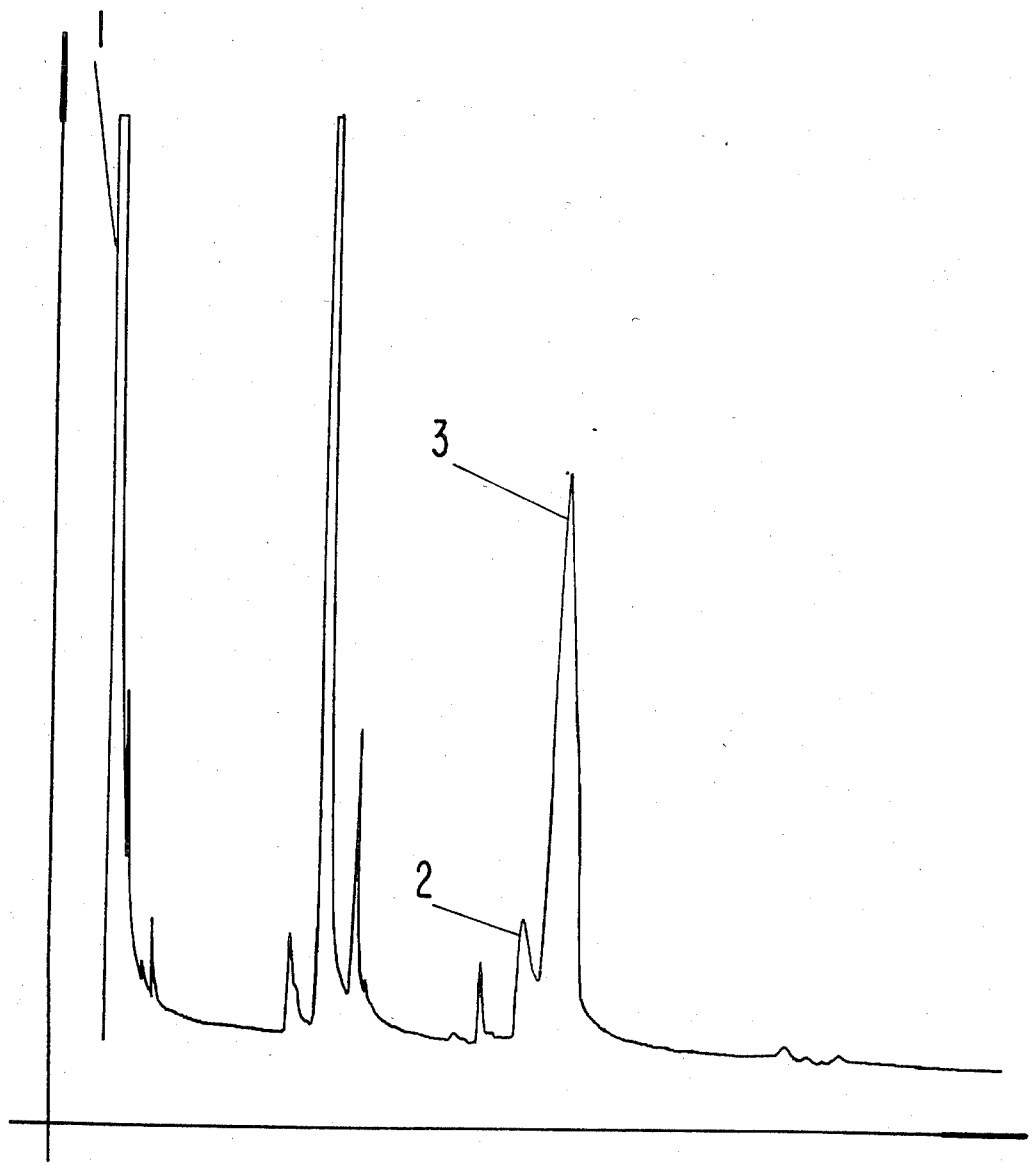
FIG. 1 is the GLC profile for the reaction product of Example II containing the compounds having the structures.

FIG. 1 is the GLC profile for the reaction product of Example II prior to hydrolysis. The peak indicated by reference numeral "1" is the peak for the compound having the structure:

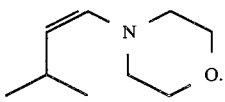

The peak indicated by reference numeral "2" is for the compound having the structure:

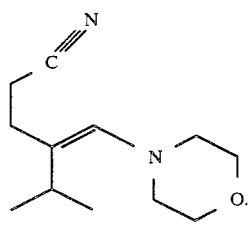

The peak indicated by the reference numeral "3" is for the compound having the structure:

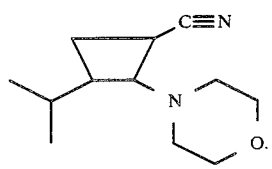

The conditions for carrying out this GLC profile are SE-30 column programmed at 100°–220° C. at 8° C. per minute.

FIG. 2 is the GLC profile for the reaction product of Example II prior to hydrolysis. The peak indicated by reference numeral "11" is the peak for the compound having the structure:

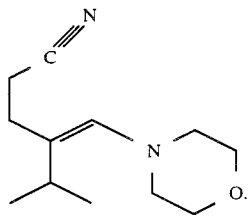

The peak indicated by the reference numeral "12" is for the compound having the structure:

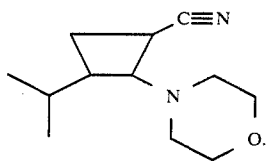

The conditions for this GLC profile are SE-30 column programmed at 100°–220° C. at 8° C. per minute.

FIG. 5 is the GLC profile for the crude reaction product of Example III. The peak indicated by reference numeral "21" is for the compound having the structure:

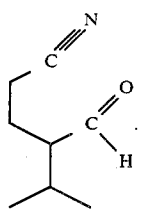

The peak indicated by reference numeral "22" is for the compound having the structure:

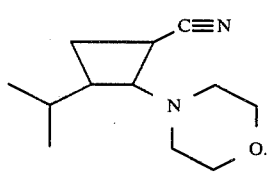

The peak indicated by reference numeral "23" is for the compound having the structure:

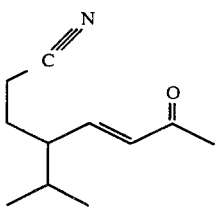

The peak indicated by reference numeral "24" is for the compound having the structure:

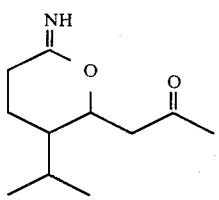

FIG. 14 is the GLC profile for bulked fractions 6–10 of the distillation product of the reaction product of Example IX (conditions: Carbowax column programmed at 100°–220° C. at 8° C. per minute). The peak indicated by reference numeral "31" is the peak for the compound having the structure:

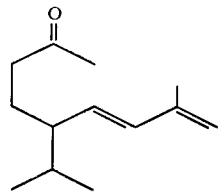

The peak indicated by reference numeral "32" is for the compound having the structure:

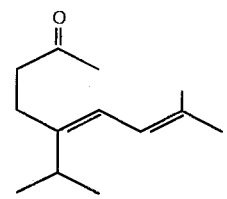

The peak indicated by reference numeral "33" is for the compound having the structure:

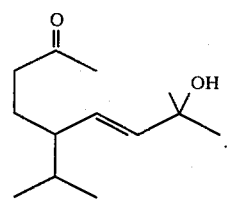

FIG. 15 is the GLC profile for the crude reaction product of Example X. The peak indicated by reference numeral "41" is for the compound having the structure:

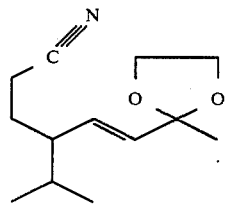

THE INVENTION

Our invention covers a process using novel chemical intermediates for preparing solanone hydrate defined according to the structures:

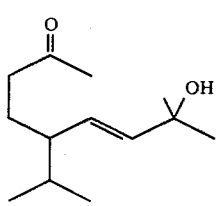

solanone, defined according to the structure:

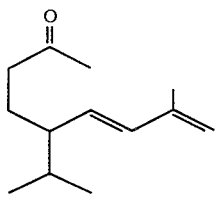

and norsolanadione having the structure:

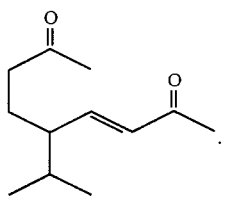

Although these compounds may be produced in substantially pure form and are so produced herein, the economics of these processes are such that the compounds are produced in admixture with other isomers thereof.

Solanone, solanone hydrate and norsolanadione are produced according to processes using novel intermediates defined according to the generic structure:

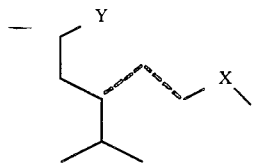

wherein X represents moieties defined according to the structures:

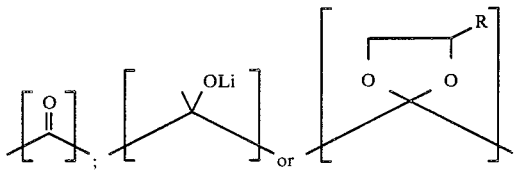

wherein R is hydrogen or methyl; and wherein Y is one of the moieties:

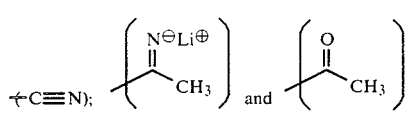

with the provisos that:
(i) when Y is the moiety having the structure:

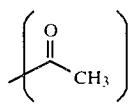

then X is the moiety having the structure:

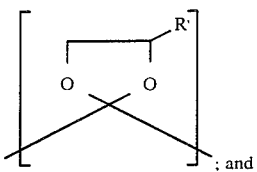

(ii) when X is the moiety having the structure:

then Y is the moiety having the structure:

$(-C\equiv N)$ and wherein one of the dashed lines is a carbon-carbon single bond and the other of the dashed lines is a carbon-carbon double bond. Examples of structures of the novel intermediates of our invention are as follows:

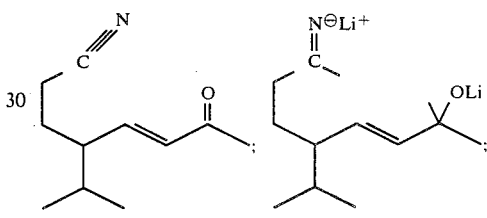

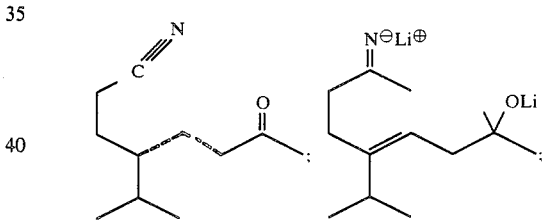

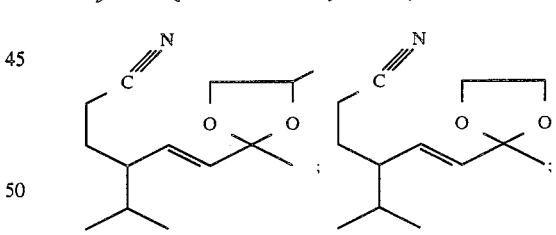

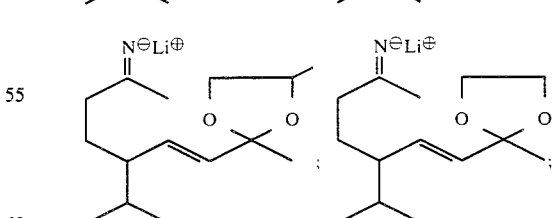

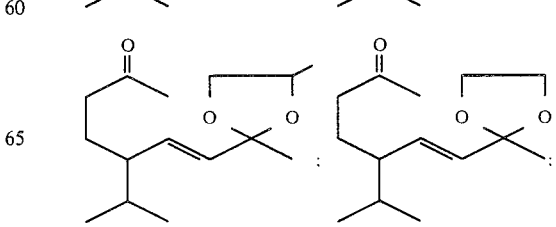

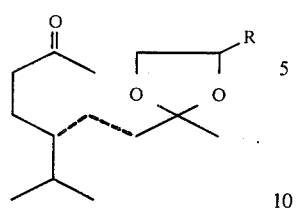

It is intended that the foregoing structures not only cover ketones in those cases but their corresponding enols as well, for example those having the structure:

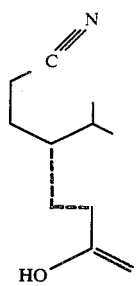

which exist in equilibrium with said ketones.

In preparing the novel intermediate having the structure:

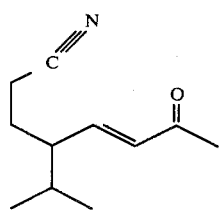

or mixture of novel intermediates having the structures:

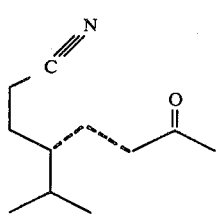

wherein in the mixture one of the dashed lines is a carbon-carbon double bond and the other of the dashed lines is a carbon-carbon single bond which intermediates are used for producing all three useful tobacco flavor augmenting or enhancing compounds, solanone, solanone hydrate and norsolanadione. Isovaleraldehyde having the structure:

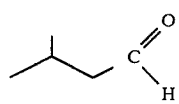

is reacted with the compound having the structure:

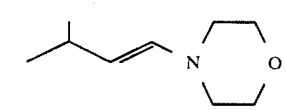

in order to produce the compound having the structure:

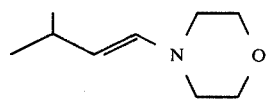

according to the reaction sequence:

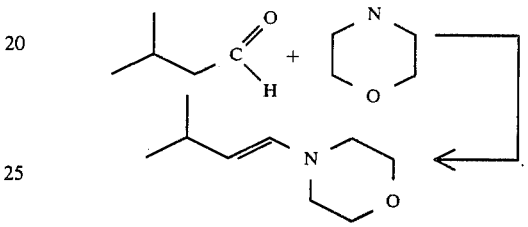

The resulting compound having the structure:

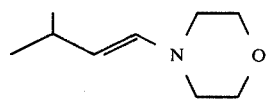

is then reacted with acrylonitrile thereby producing two compounds having the structures:

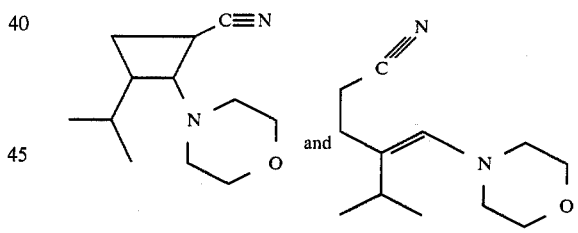

according to the reaction sequence:

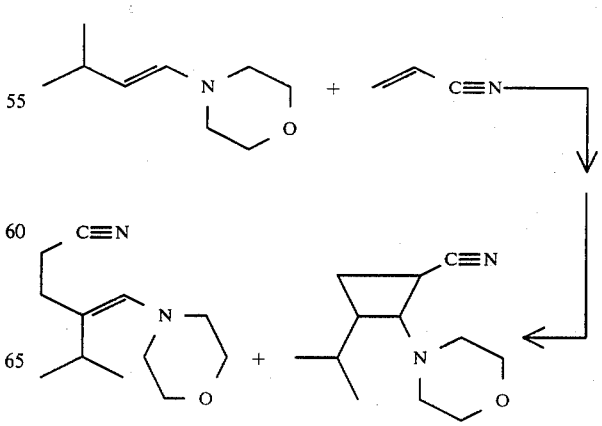

The compounds having the structures:

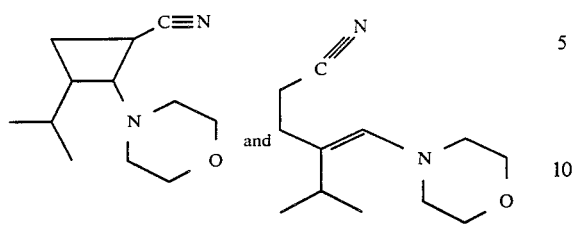

and are then hydrolyzed to produce the aldehyde defined according to the structure:

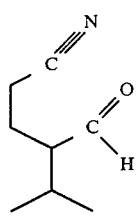

as well as the starting material having the structure:

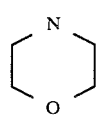

according to the reaction sequence:

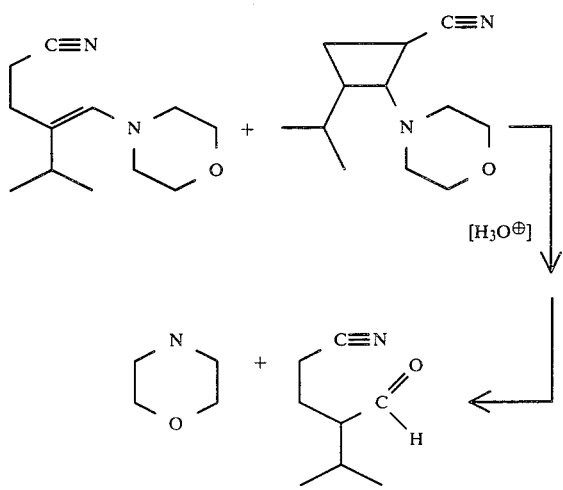

The resulting aldehyde having the structure:

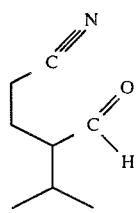

is then reacted with acetone via an aldol condensation reaction thereby forming a mixture of ketones having the structures:

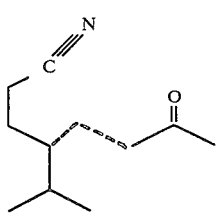

which can be separated into its component compounds or retained "as is". The desired component compound of the mixture having the structure:

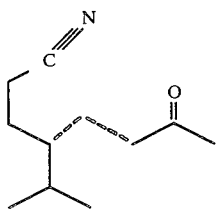

is the compound having the structure:

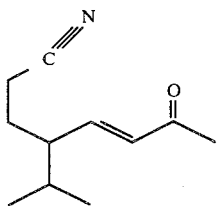

(wherein in the mixture one of the dashed lines is a carbon-carbon double bond and the other of the dashed lines is a carbon-carbon single bond).

This reaction is as follows:

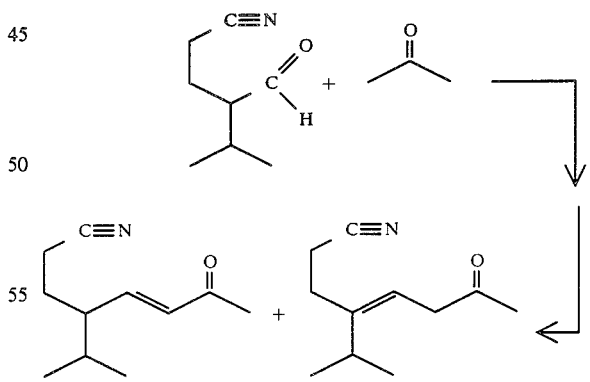

The aldol condensation for the reaction of acetone with the aldehyde is carried out using the standard aldol condensation basic catalyst such as sodium hydroxide, potassium hydroxide, barium hydroxide or calcium hydroxide at temperatures in the range of from about 30° C. up to about 60° C. The most preferred catalyst is barium hydroxide. The mole ratio of the aldehyde:acetone may vary from about 1:6 to about 1:1 aldehyde-:acetone. When using a sodium hydroxide catalyst, it is preferred that the temperature of reaction be about 50°–60° C. When using potassium hydroxide, it is preferred that the reaction temperature be 30°–45° C. When using barium hydroxide, it is preferred that the reaction temperature be 45°–60° C.

The mole ratio of base, e.g. sodium hydroxide, potassium hydroxide, barium hydroxide or calcium hydroxide:aldehyde reactant may vary from about 0.05:1 up to about 1:1. Actually, the aldol condensation reaction is a two-step reaction; the first reaction producing the actual "aldol" and the second reaction to produce the unsaturated keto-nitrile mixture having the structure:

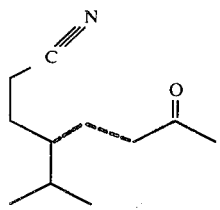

wherein in the mixture, in each of the compounds, one of the dashed lines is a carbon-carbon double bond and the other of the dashed lines is a carbon-carbon single bond:

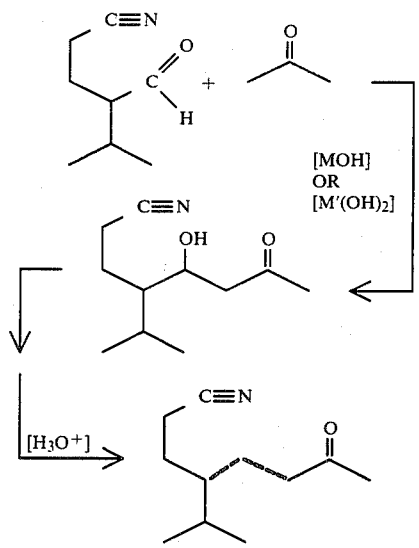

wherein M is alkali metal and M' is alkaline earth metal and wherein one of the dashed lines in the compounds of the mixture formed is a carbon-carbon double bond and the other of the dashed lines in the compounds of the mixture formed is a carbon-carbon single bond. Accordingly, the "aldol" intermediate having the structure:

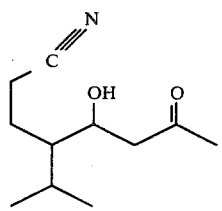

is also contemplated as one of the novel intermediates of this invention. In carrying out the dehydration of the compound having the structure:

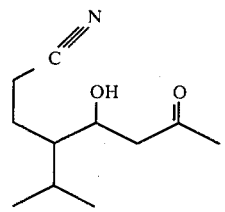

in order to form the compounds defined according to the structure:

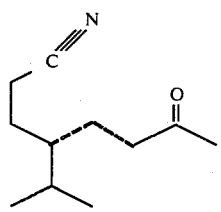

(mixture, wherein in the mixture in each of the molecules, one of the dashed lines is a carbon-carbon double bond and the other of the molecules is a carbon-carbon single bond). Examples of acids which can be used are acetic acid and oxalic acid. Thus, the ionization constant of the acid must be sufficient to dehydrate the hydroxyl group yet not hydrolyze the nitrile moiety. More specifically, the hydronium ion concentration must be high enough to give rise to a dehydration but low enough not to hydrolyze the nitrile moiety to a carboxylic acid.

In producing solanone from the compound having the structure:

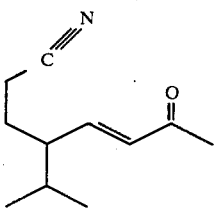

or from the mixture of compounds defined according to the structure:

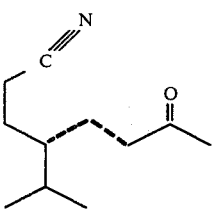

the nitrile ketone is first reacted with methyl lithium to form an organometallic intermediate defined according to the structure:

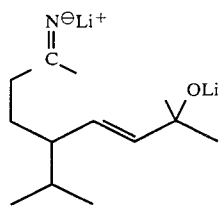

This organometallic intermediate is then hydrolyzed in the presence of acid to form solanone hydrate defined according to the structure:

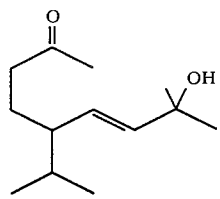

taken alone or in admixture with the compound defined according to the structure:

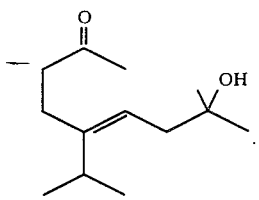

As stated in the "Background of the Invention", solanone hydrate is a known tobacco flavorant and is useful in augmenting or enhancing the aroma or taste of smoking tobacco both prior to and on smoking in the main stream and the side stream. The solanone hydrate thus can be used "as is" or can be dehydrated to form compounds defined according to the structures:

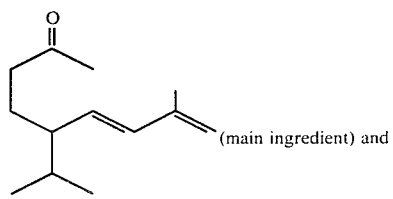 (main ingredient) and

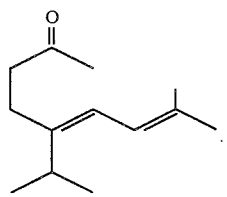

A small amount of the compound defined according to the structure

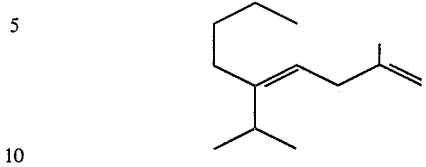

is also formed from dehydration of the compound having the structure:

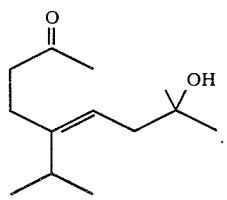

In carrying out the reaction of the compound having the structure:

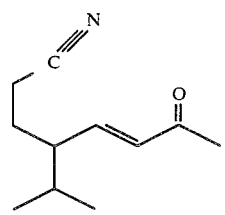

or the mixture of compounds defined according to the structure:

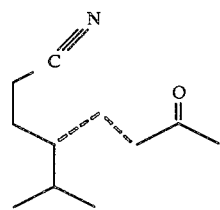

in order to produce the intermediate defined according to the structure:

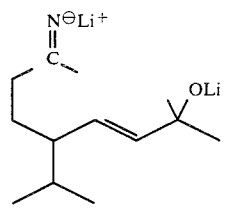

or the mixture of intermediates defined according to the structures:

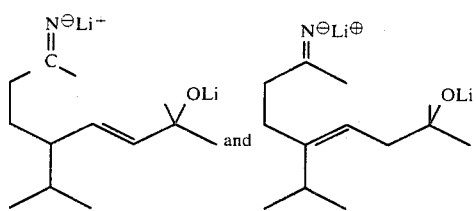

according to the reaction, for example:

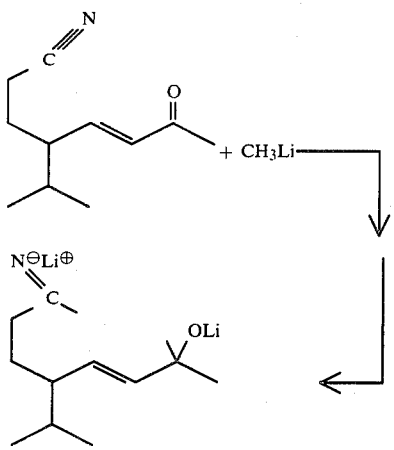

the methyl lithium is preferably formed in situ as by reaction of lithium metal with methyl bromide in the presence of an inert solvent such as anhydrous diethylether. The reaction of the methyl lithium with the nitrile having the structure:

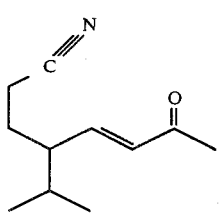

or the mixture of nitriles having the structure:

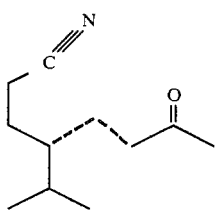

preferably takes place in the presence of an inert solvent such as toluene or xylene. The temperature of reaction may vary from about 0° C. up to about 60° C. but most preferably and conveniently, the temperature of reaction is at ambient conditions, e.g. 20°-30° C. at atmospheric pressure. There is no need to operate the reaction at pressures higher or lower than atmospheric since no increase in the yield or conversion occurs at higher or lower pressures. The mole ratio of methyl lithium:nitrile having the structure:

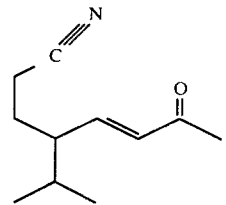

or nitrile mixture defined according to the structure:

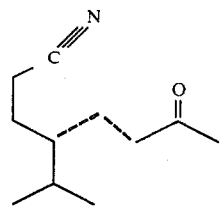

may vary from about 1:1 methyl lithium:nitrile up to about 5:1 methyl lithium:nitrile with an excess of methyl lithium being preferred.

The hydrolysis reaction, for example:

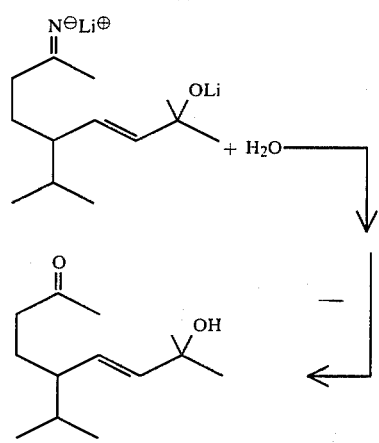

is carried out in the presence of water and a weak protonic acid such as dilute sulfuric acid and dilute phosphoric acid, dilute ammonium chloride, or dilute hydrochloric acid or mixtures of same. In the hydrolysis reaction, it is necessary to use sufficient aqueous acid such that a complete hydrolysis of the organometallic intermediates defined according to the structures:

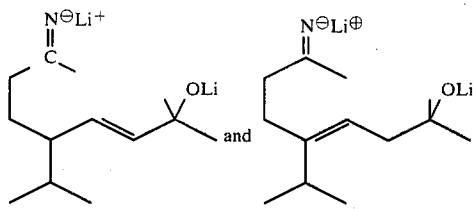

occurs. At the end of the reaction, the solvents are stripped from the reaction mass, e.g. the diethylether and toluene remaining, and the reaction product is fractionally distilled in order to either (a) insure a pure enough product for use as a tobacco flavorant or (b) in order to insure a pure enough product for the subsequent reaction to form the solanone compound or mixture of compounds.

The dehydration of the compound defined according to the structure:

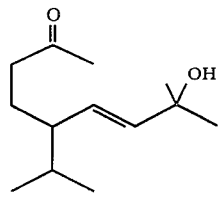

or the mixture of compounds defined according to the structures:

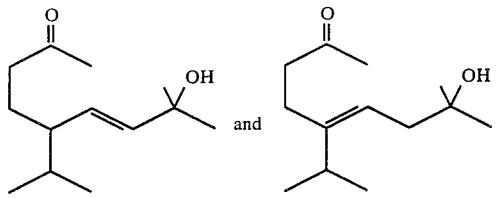

is carried out according to the reaction, for example:

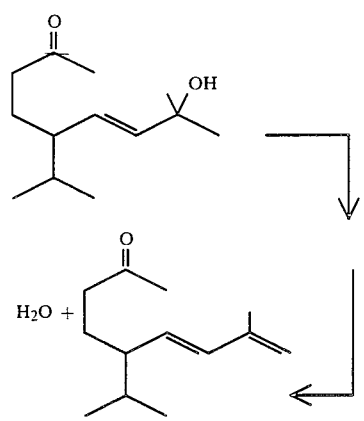

The dehydration reaction is carried out in the presence of a dehydrating agent, for example, phosphorous oxychloride in a pyridine solvent. The mole ratio of solanone hydrate:dehydrating agent may vary from about 1:1 solanone hydrate:dehydrating agent up to about 4:1 solanone hydrate:dehydrating agent. Obviously, where the excess of solanone hydrate is used, the unreacted distilled solanone hydrate is recycled. Other dehydrating agents usable may be anhydrous aluminum chloride or concentrated sulfuric acid.

The dehydration reaction is carried out at a temperature in the range of from about 30° C. up to about 120° C. with a preferred reaction temperature being in the range of from 50° C. up to 100° C. At the end of the reaction, the reaction mass is "worked-up" by means of standard extraction, neutralization, drying and fractional distillation.

In using the nitrile intermediate defined according to the structure:

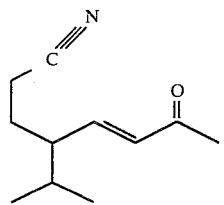

or the mixture of nitrile intermediates defined according to the structure:

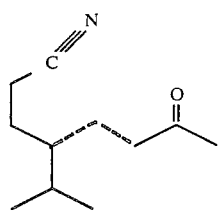

to produce the norsolanadione defined according to the structure:

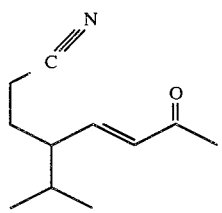

the ketone moiety is first "ketalized" to form a ketal or a mixture of ketals defined according to the structure:

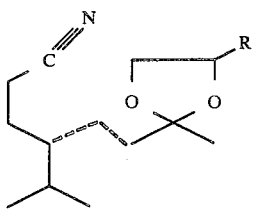

wherein one of the dashed lines is a carbon-carbon double bond and the other of the dashed lines is a carbon-carbon single bond and wherein R represents hydrogen or one of $C_1$–$C_4$ alkyl. This "ketalization" reaction; for example:

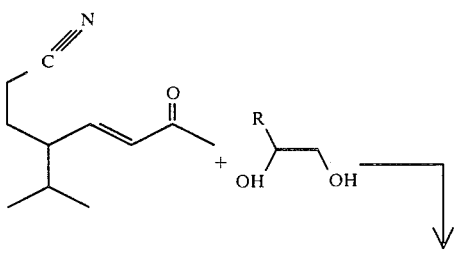

-continued

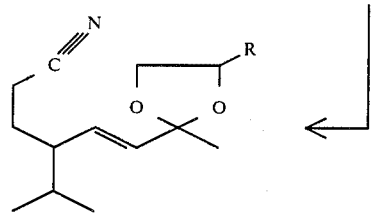

is carried out using, for example, ethylene glycol (wherein R is hydrogen); 1,2-propylene glycol (wherein R is methyl) or 1,2-butylene glycol (wherein R is ethyl). Other ketals can be formed but these would be uneconomical, for example, ketals formed from 2,3-butylene glycol or 2,3-pentylene glycol.

The temperature of the "ketalization" reaction is preferably between 25° C. and 45° C. The ketalization reaction is carried out in the presence of an acid such as sulfuric acid or an acid ion exchange resin, e.g. a polystyrene sulfonic acid such as Amberlyst ® 15 manufactured by the Rohm & Haas Corporation of Philadelphia, Pa. or paratoluene sulfonic acid. It is preferable to carry out the ketalization reaction in the presence of an additional reagent, trimethylorthoformate. Thus, the acidic reagent is preferably formed from mixing trimethylorthoformate and, for example, Amberlyst ® 15. Then the reactants, for example, ethylene glycol or propylene glycol are admixed with the ketone nitrile defined according to the structure:

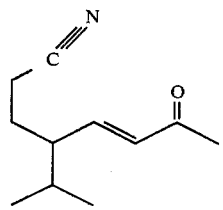

or mixture of same defined according to the structure:

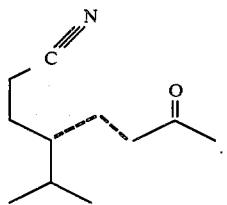

Other acids which may be used in the ketalization reaction are Lewis acids such as borontrifluoride diethyletherate, stannic chloride or zinc chloride with borontrifluoride diethyletherate being preferred. The mole ratio of ketone defined according to the structure:

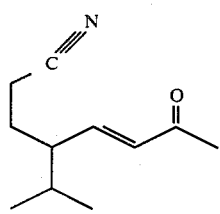

or mixture of ketones defined according to the structure:

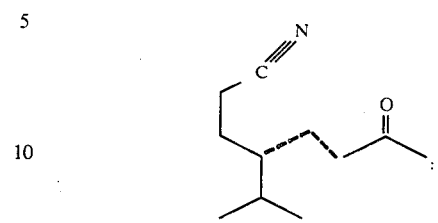

glycol such as ethylene glycol or propylene glycol may vary from about 0.8:1 up to about 1:0.8 with a preferred mole ratio of 1:1. In summary, the ketalization reaction may be carried out in the presence of protonic acids such as hydrochloric acid or ion exchange catalysts such as Amberlyst ® 15 or Lewis acids such as borontrifluoride diethyletherate or the like. At the end of the reaction, the reaction mass is stripped of solvent and fractionally distilled in order to insure a substantially pure enough ketal to carry out the subsequent reaction leading to the formation of the norsolanadione.

Thus, in the next step of the reaction, the resulting ketal or mixture of ketals defined according to the structure:

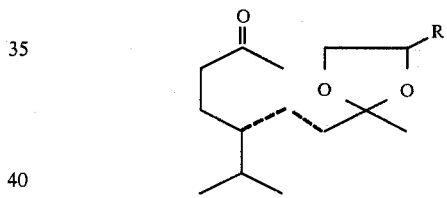

is reacted with methyl lithium according to the reaction, for example:

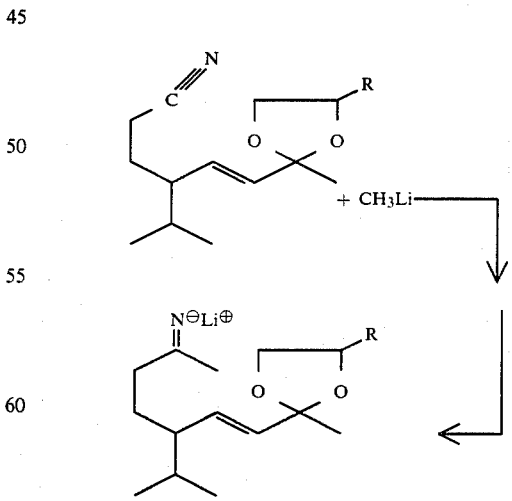

wherein R represents hydrogen or $C_1$-$C_4$ alkyl in order to form novel organometallic intermediates, for example those defined according to one of the structures:

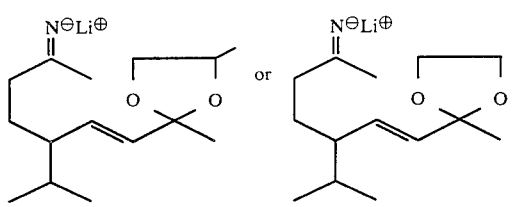

The temperature of reaction may vary from about −10° C. up to about +20° C. The reaction takes place in the presence of an inert volatile solvent such as diethylether or tetrahydrofuran. The mole ratio of methyl lithium:-ketal derivative may vary from about 0.5:1 up to about 1:4. At the end of the reaction, the reaction product is hydrolyzed in the presence of a protonic acid such as dilute hydrochloric acid, dilute sulfuric acid or dilute aqueous ammonium chloride at a temperature in the range of from about 0° C. up to about 50° C.; most conveniently at ambient conditions; 20°-30° C. and atmospheric pressure according to the reaction; for example:

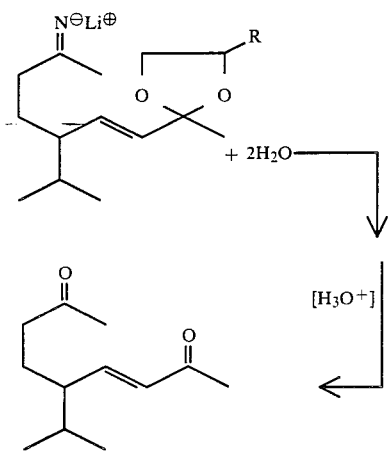

wherein R is defined supra. The reaction mass is then "worked-up" as by extraction and fractional distillation in order to form a pure, organoleptically acceptable and toxicologically acceptable derivative useful in augmenting or enhancing the aroma or taste of smoking tobacco both prior to and on smoking.

During the step of hydrolysis of the organometallic ketal species defined generally according to the structure:

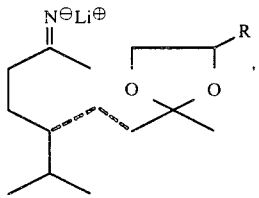

although the major compound formed is norsolanadione defined according the the generic structure:

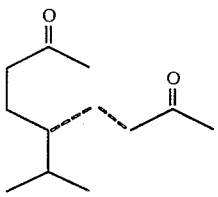

(a mixture, wherein in the mixture one of the dashed lines is a carbon-carbon double bond and the other of the dashed lines is a carbon-carbon single bond) there is also formed a mixture of compounds defined according to the structure:

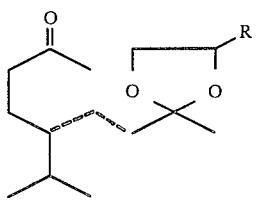

wherein in the mixture, one of the dashed lines is a carbon-carbon double bond and the other of the dashed lines is a carbon-carbon single bond and R represents hydrogen or $C_1$-$C_4$ alkyl. This mixture is usually separated from the reaction mass as by distillation and the components may be separated from one another by fractional distillation in vacuuo. The resulting components are useful as intermediates for forming solanadione in and of themselves, or they may be used as such for augmenting or enhancing the aroma or taste of smoking tobaccos.

Furthermore, the ketals of our invention which are defined according to the structure:

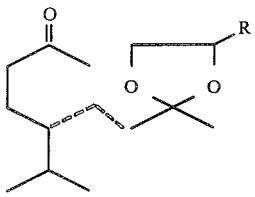

wherein R represents hydrogen or $C_1$-$C_4$ alkyl and one of the dashed lines represents a carbon-carbon double bond and the other of the dashed lines represents a carbon-carbon single bond including the compounds defined according to the structures:

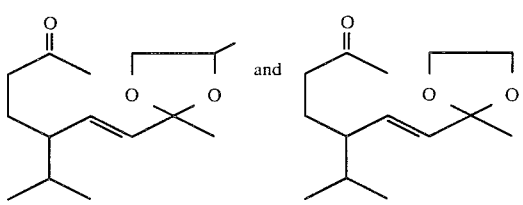

(hereinafter referred to as "keto ketals" produces as by-products of our invention are capable of supplying and/or potentiating certain flavor and aroma notes usually lacking in many tobacco flavors heretofore provided.

As used herein in regard to tobacco flavors, the terms "alter" and "modify" in their various forms means "supplying or imparting flavor character or note to otherwise bland tobacco, tobacco substituents, or tobacco flavor formulations or augmenting the existing flavor characteristics where a natural flavor is deficient in some regard or supplementing the existing flavor impression to modify its quality, character or taste".

As used herein, the term "enhance" is intended to mean the intensification (without change in kind of quality of aroma or taste) of one or more taste and/or aroma nuances present in the organoleptic impression of tobacco or a tobacco substitute or a tobacco flavor.

Our invention thus provides an organoleptically improved smoking tobacco product and additives therefor, as well as methods of making the same which overcome specific problems heretofore encountered in which specific desired Virginia-type tobacco aroma and taste nuances thereof, are created or enhanced and may be readily controlled and maintained at the desired uniform level regardless of variations in the tobacco components of the blend.

This invention further provides improved tobacco additives and methods whereby various Virgina-type tobacco notes may be imparted to smoking tobacco products and may be readily varied and controlled to produce the desired uniform flavor characteristics.

In carrying out this aspect of our invention, we add to smoking tobacco materials or a suitable substitute therefor (e.g. dried lettuce leaves) an aroma and flavor additive containing as an active ingredient a keto ketal(s) produced according to the process of our invention.

In addition to the keto ketal(s) produced according to the process of our invention, other flavoring and aroma additives may be added to the smoking tobacco materials or substitute therefor, either separately or in mixture with the keto ketal(s) produced according to the process of our invention, as follows:

(i) Synthetic materials:
Beta-ethyl-cinnamaldehyde;
Beta-cyclohomocitral;
Eugenol;
Dipentene;
Beta-damascenone;
Beta-damascone;
Maltol;
Ethyl maltol;
Delta-undecalactone;
Delta-decalactone;
Benzaldehyde;
Amyl acetate;
Ethyl butyrate;
Ethyl valerate;
Ethyl acetate;
2-hexenol-1;
2-methyl-5-isopropyl-1,3-nonadiene-8-one;
2,6-dimethyl-2,6-undecadiene-10-one;
2-methyl-5-isopropyl acetophenone;
2-hydroxy-2,5,5,8a-tetramethyl-1-(2-hydroxyethyl)-decahydronaphthalene;
Dodecahydro-3a,6,6,9a-tetramethylnaphtho[2,1,b]-furan;
4-hydroxy hexanoic acid, gamma lactone and polyisoprenoid hydrocarbons defined in Example V of U.S. Pat. No. 3,589,372, issued on June 29, 1971.
(ii) Natural oils:
Celery seed oil;
Coffee extract;
Bergamot oil;
Cocoa extract;
Nutmeg oil;
Origanum oil.

An aroma and flavoring concentrate containing keto ketal(s) produced according to the process of our invention and, if desired, one or more of the above-indicated additional flavoring additives may be added to the smoking tobacco material, to the filter or to the leaf or paper wrapper. The smoking tobacco material may be shredded, cured, cased and blended tobacco material or reconstituted tobacco material or tobacco substitutes (e.g. lettuce leaves) or mixtures thereof. The proportions of flavoring additives may be varied in accordance with taste but insofar as enhancement or the imparting of natural and/or sweet notes, we have found that satisfactory results are obtained if the proportion by weight of the sum total of the keto ketal(s) produced according to the process of our invention to smoking tobacco material is between 250 ppm and 1,500 ppm (0.025%–0.15%) of the active ingredients to the smoking tobacco material. We have further found that satisfactory results are obtained if the proportion by weight of the sum total of the keto ketal(s) produced according to the process of our invention used to flavoring material is between 2,500 and 15,000 ppm (0.25%–1.5%).

Any convenient method for incorporating the keto ketal(s) produced according to the process of our invention in the tobacco product may be employed. Thus, the keto ketal(s) produced according to the process of our invention taken alone or along with other flavoring additives may be dissolved in a suitable solvent such as ethanol, pentane, diethylether and/or other volatile organic solvents and the resulting solution may either be sprayed on the cured, cased and blended tobacco material or the tobacco material may be dipped into such solution. Under certain circumstances, a solution of the keto ketal(s) produced according to the process of our invention taken alone or taken further together with other flavoring additives as set forth above, may be applied by means of a suitable applicator such as a brush or roller on the paper or leaf wrapper for the smoking product, or it may be applied to the filter by either spraying or dipping or coating.

Furthermore, it will be apparent that only a portion of the tobacco or substitute therefore need be treated and the thus treated tobacco may be blended with other tobaccos before the ultimate tobacco product is formed. In such cases, the tobacco treated may have the keto ketal(s) produced according to the process of our invention in excess of the amounts or concentrations above indicated so that when blended with other tobaccos, the final product will have the percentage within the indicated range.

In accordance with one specific example of our invention, an aged, cured and shredded domestic burley tobacco is sprayed with a 20% ethyl alcohol solution of a 50:50 (mole:mole) ratio of compounds defined according to the structures:

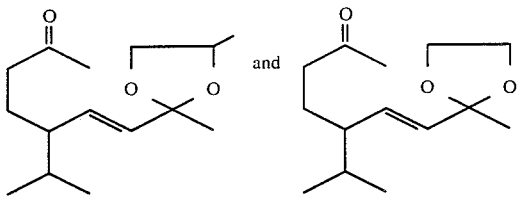

and in an amount to provide a tobacco composition containing 800 ppm by weight of the keto ketal mixture on a dry basis. Thereafter the alcohol is removed by evaporation and the tobacco is manufactured into cigarettes by the usual techniques. The cigarettes, when treated as indicated, have desired and pleasing aroma (increased smoke body sensation in the mouth with enhanced tobacco-like notes and pleasant aromatic nuances) which is detectable in the main and side streams when the cigarette is smoked. This aroma is described as having sweet, fruity, Virginia tobacco-like notes.

While our invention is particularly useful in the manufacture of smoking tobacco such as cigarette tobacco, cigar tobacco and pipe tobacco, other tobacco products formed from sheeted tobacco dust or fines may also be used. Likewise, the keto ketal(s) produced according to the process of our invention can be incorporated with materials such as filter tip material, seam paste, packaging materials and the like which are used along with tobacco to form a product adapted for smoking. Furthermore, the keto ketal(s) produced according to the process of our invention can be added to certain tobacco substitutes of natural or synthetic origin (e.g. dried lettuce leaves) and, accordingly, by the term "tobacco" as used throughout this specification is meant any composition intended for human consumption by smoking or otherwise, whether composed of tobacco plant parts or substitute materials or both.

The following examples serve to illustrate our invention and the invention is to be considered restricted thereto only as indicated in the appended claims.

All parts and percentages given herein are by weight unless otherwise specified.

EXAMPLE I

Preparation of 4-(3-methyl-1-butenyl) morpholine

Reaction:

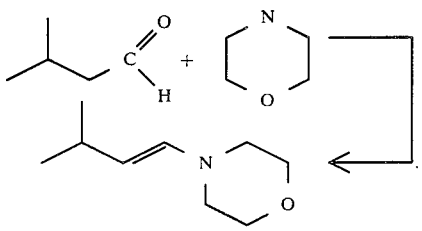

Into a 12 liter flask equipped with stirrer, Bidwell trap, thermometer, heating mantle, addition funnel and condenser is placed 2,200 ml of cyclohexane and 2,180 grams (25 moles) of morpholine. The resulting mixture is heated to 50° C. and 2,155 grams of isovaleraldehyde are added over a 1.5 hour period. An exotherm occurs and the solution begins to reflux. Additional heat is applied and the refluxing is continued until no additional water is collected in the Bidwell trap. The cyclohexane is then stripped off and the reaction product is distilled through a 1" stone packed column at total take-off yielding the following fractions:

| Fraction Number | Vapor Temp. (°C.) | Liquid Temp. (°C.) | Vacuum mm/Hg. | Weight of Fraction (grams) |
|---|---|---|---|---|
| 1 | 55/70 | 80/90 | 4 | 51 |
| 2 | 75 | 95 | 4 | 442 |
| 3–9 | 80 | 95/140 | 4 | 2855 |
| 10 | 80 | 175 | 4 | 254 |

Fractions 3–9 are bulked for use in Example II.

EXAMPLE II

Preparation of 4-isopropylglutaraldehydonitrile

Reactions:

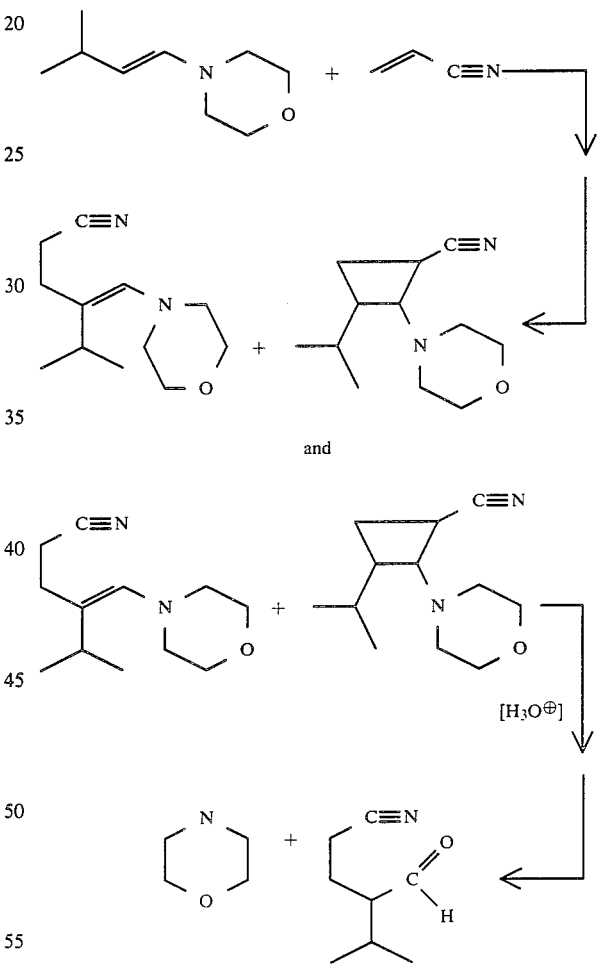

Into a 22 liter flask equipped with stirrer, condenser, thermometer, heating mantle, addition funnel and nitrogen blanked is placed 2,855 grams of bulked fractions 3–9 of the distillation product of the reaction product of Example I, the 4-(3-methyl-1-butenyl)morpholine and 3,600 ml anhydrous ethyl alcohol. The resulting mixture is stirred and heated to reflux. 1,456 grams (27.4 moles) of acrylonitrile is added to the reaction mass over a period of 1.5 hours. Reflux is continued until a GLC profile shows that more than 95% of the enamine has converted to product.

FIG. 1 is the GLC profile for the reaction mass at this point; prior to hydrolysis. The conditions are: SE-30 column programmed at 100°-220° C. at 8° C. per minute. The peak indicated by reference numeral "1" is the peak for the starting material having the structure:

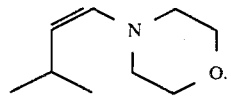

The peak indicated by reference numeral "2" is the peak for the reaction product having the structure:

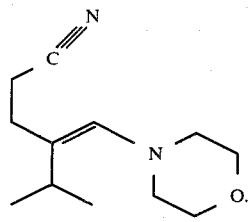

The peak indicated by reference numeral "3" is the peak for the compound defined according to the structure:

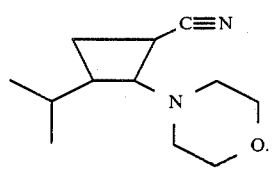

Reflux is continued and 4,600 ml of 5% aqueous hydrochloric acid is added to the reaction mass over a 40 minute period. The reflux is continued and the reaction is monitored by GLC until no change is apparent (20 hours). The enamine adduct converts to product and the cyclobutane adduct converts to product over a somewhat longer period of time. When the reaction is complete, three liters of water is added to the reaction mass resulting in two phases, an organic phase and an aqueous phase. The organic phase is separated from the aqueous phase. The aqueous phase is washed once with one liter of dichloromethane and the organic phases are combined. The organic phases are stripped of solvent and distilled on a 1" Goodloe packed column at a 9:1 reflux ratio yielding the following fractions:

| Fraction Number | Vapor Temp. (°C.) | Liquid Temp. (°C.) | Vacuum mm/Hg. | Weight of Fraction (grams) |
|---|---|---|---|---|
| 1 | 60/65 | 120 | 3.8 | 31 |
| 2 | 99 | 122 | 3.5 | 33 |
| 3 | 99 | 134 | 3.5 | 106 |
| 4-11 | 100/112 | 139/141 | 3.5 | 1869 |
| 12-14 | 105/90 | 141/225 | 3.0 | 775 |

Fractions 4-11 are bulked to yield 1,869 grams of product of 83% purity which is used in Example III, infra.

FIG. 2 is the GLC profile for the reaction product at the end of the reaction and prior to hydrolysis (conditions: SE-30 column programmed at 100°-220° C. at 8° C. per minute). The peak indicated by reference numeral "11" is the peak for the compound having the structure:

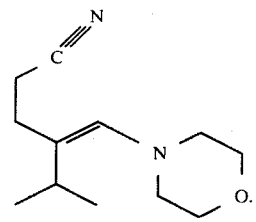

The peak indicated by reference numeral "12" is for the compound having the structure:

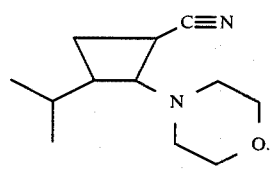

FIG. 3 is the GLC profile for the reaction product subsequent to hydrolysis containing the compound defined according to the structure:

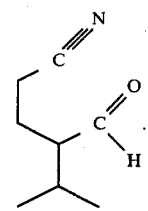

FIG. 4A is the GLC profile for the distillation product of the reaction product of Example II, bulked fractions 4-11 containing the compound having the structure:

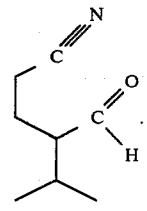

FIG. 4B is the GLC profile for fraction 2 of the distillation product of the reaction product of Example II containing the compound having the structure:

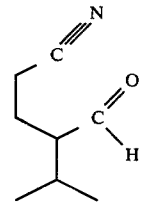

(conditions: 10'×⅛" SE-30 column programmed at 150°-220° C. at 8° C. per minute).

EXAMPLE III

Preparation of 4-isopropyl-7-oxo-5-octenenitrile

Reaction:

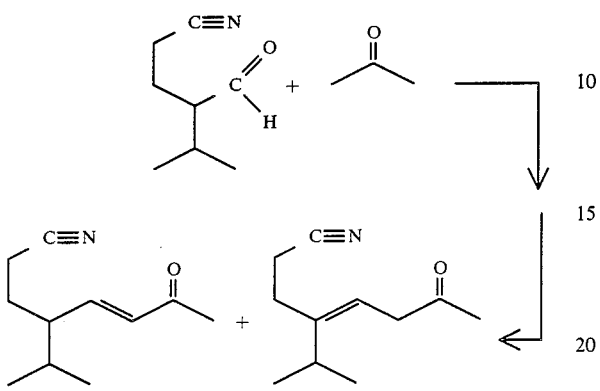

Into a 2-liter flask equipped with stirrer, condenser, thermometer, heating mantle, Buchner funnel and Bidwell apparatus is placed 496 grams (2.9 moles) of 4-isopropylglutaraldehydonitrile, bulked fractions 4-11, prepared according to the procedure of Example II; 850 grams (14.7 moles) of acetone and 100 grams (0.59 moles) of barium hydroxide monohydrate.

The resulting mixture is stirred and heated to reflux and refluxed for a period of 10 hours. After cooling to room temperature, the reaction mass is filtered to remove the barium hydroxide. The excess acetone is removed from the reaction mass in vacuum (150 mm/Hg vacuum). The resulting crude oil weight is 592 grams.

The residual oil is placed in a 2-liter flask equipped with a Bidwell trap and reflux condenser. 600 ml toluene and 20 grams of oxalic acid are then added to the reaction mixture and the resulting mixture is heated to reflux for a period of 2 hours until no more water is evolved. After cooling, the resulting reaction mass is washed with 600 ml water followed by 500 ml of a saturated sodium bicarbonate solution followed by 500 ml of a saturated sodium chloride solution.

The crude reaction product is then stripped of solvent and distilled on a 2.5" Splash column yielding the following fractions:

| Fraction Number | Vapor Temp. (°C.) | Liquid Temp. (°C.) | Pressure mm/Hg. | Weight of Fraction (grams) | Product % |
|---|---|---|---|---|---|
| 1 | 98-105 | 129-132 | 1 | 14.4 | 44 |
| 2 | 105-120 | 132-143 | 1 | 42.8 | 73 |
| 3 | 120-127 | 143-153 | 1 | 131.4 | 91 |
| 4 | 127-150 | 153-193 | 1 | 98.4 | 94 |
| 5 | 150-190 | 193-238 | 1 | 40.4 |  |

FIG. 5 is the GLC profile for the crude reaction product after refluxing for 10 hours (conditions: 10'×⅛" SE-30 column programmed at from 150°-220° C. at 8° C. per minute). The peak indicated by reference numeral "21" on FIG. 5 is for the compound defined according to the structure:

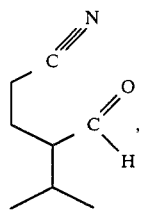

the starting material.

The peak indicated by reference numeral "22" is for the compound defined according to the structure:

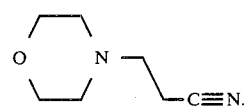

The peak indicated by reference numeral "23" is for the product defined according to the structure:

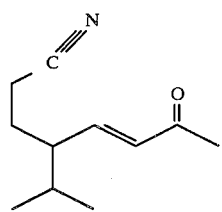

The peak indicated by reference numeral "24" is for the product having the structure:

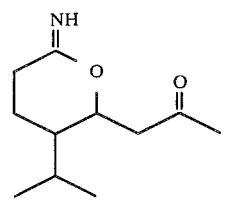

FIG. 6 is the GLC profile for bulked fractions 1-4 of the distillation product of the reaction product of this example (conditions: SE-30 10'×⅛" column programmed at 150°-220° C. at 8° C. per minute).

EXAMPLE IV

Preparation of 4-isopropyl-7-oxo-5-octenenitrile

Reaction:

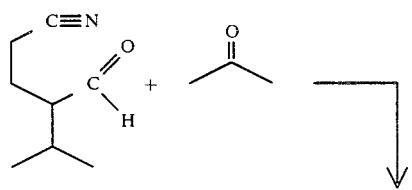

-continued

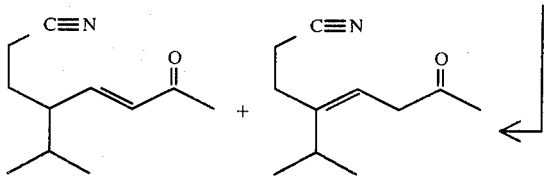

Into a 500 cc reaction vessel equipped with stirrer, condenser, thermometer, and heating mantle is placed 1.0 moles of gluteraldehydonitrile (bulked fractions 4–11 of Example III); 2.0 moles of acetone and 0.05 liters of a one molar aqueous solution of sodium hydroxide. The reaction mass is stirred for a period of five hours and then heated at 50°–60° C. for an additional five hours. The reaction mass is then cooled to room temperature and 200 cc of water is added with stirring. The reaction mass is then neutralized with a 50% aqueous solution of acetic acid. The organic phase is separated from the aqueous phase and the organic phase is washed with two 200 cc portions of water followed by one 200 cc portion of 10% sodium bicarbonate solution. The reaction mass is dried over anhydrous magnesium sulfate and stripped of solvent. The reaction mass is then distilled on a 12" stone-packed column yielding the following fractions:

| Fraction Number | Vapor Temp. (°C.) | Liquid Temp. (°C.) | Pressure mm/Hg. | Weight of Fraction (grams) |
|---|---|---|---|---|
| 1 | 50/90 | 120/140 | 0.5/0.4 | 11.0 |
| 2 | 135 | 155 | 0.4 | 22.0 |
| 3 | 138 | 189 | 0.6 | 40.0 |
| 4 | 178 | 250 | 0.7 | 14.0 |

EXAMPLE V

Preparation of 4-isopropyl-7-oxo-7-octenenitrile

Reaction:

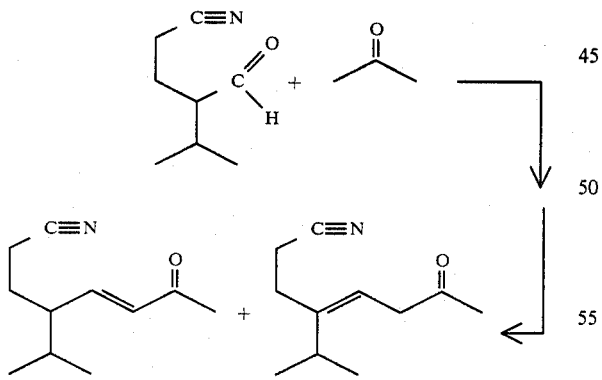

Into a 2-liter reaction vessel equipped with stirrer, condenser, thermometer, dropping funnel and heating mantle is placed 250 ml anhydrous methanol and 5 grams (0.089 moles) of potassium hydroxide pellets. The potassium hydroxide is dissolved in the methanol. From the dropping funnel, 137.0 grams (1.0 moles) of glutaraldehydonitrile (bulked fractions 4–11 of Example III) is added over a period of 0.5 hours. The reaction mass temperature is at 30° C. and is heated to 40° C. While maintaining the reaction mass at 40° C., from the dropping funnel, 174 grams (3.0 moles) of acetone is added to the reaction mass from the dropping funnel.

The reaction mass is then refluxed for a period of three hours and GLC analysis indicates that the reaction is complete. The reaction mass is then cooled to room temperature and 200 cc of water is added. The reaction mass is then neutralized with a 50% aqueous solution of acetic acid (25 ml). The reaction mass is extracted with diethylether and the diethylether extracts are washed with two 100 cc portions of water followed by one 100 cc portion of sodium bicarbonate solution. The resulting material is dried over anhydrous magnesium sulfate, stripped of solvent and distilled on a 2" Splash column yielding the following fractions:

| Fraction Number | Vapor Temp. (°C.) | Liquid Temp. (°C.) | Pressure mm/Hg. | Weight of Fraction (grams) |
|---|---|---|---|---|
| 1 | 100/120 | 145/175 | 2.0/5.0 | 11.0 |
| 2 | 135 | 200 | 5.0 | 24.0 |
| 3 | 140 | 240 | 5.0 | 1.0 |

FIG. 7A is the GLC profile for the crude reaction product containing the compound having the structure:

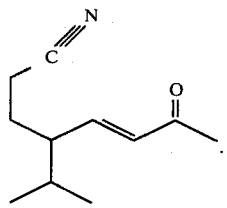

FIG. 7B is the GLC profile for the distillation product of the foregoing distillation (conditions: SE-30 column programmed at 100°–220° C. at 8° C. per minute). This material contains the compound having the structure:

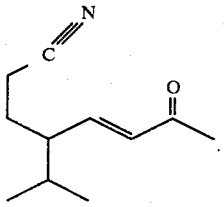

FIG. 8 is the infra-red spectrum for the compound having the structure:

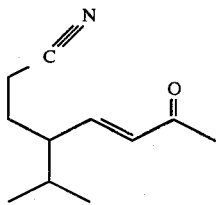

produced according to this example.

EXAMPLE VI

Preparation of 4-isopropyl-7-oxo-7-octenenitrile

Reaction:

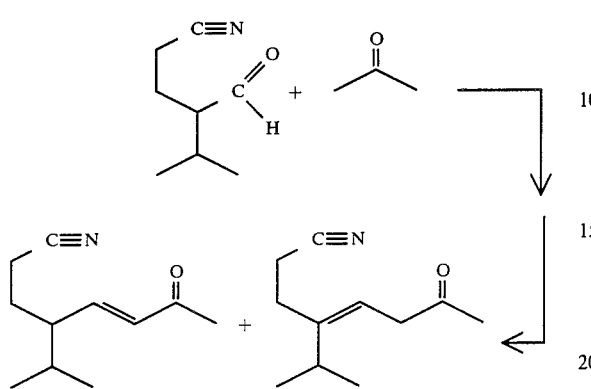

Into a 500 cc reaction flask equipped with stirrer, condenser, thermometer and heating mantle is placed 66 cc of a one-molar aqueous solution of sodium hydroxide and 154.0 grams (1.125 moles) of glutaraldehydonitrile (bulked fractions 4-11 of Example III). From the dropping funnel, 130.5 grams (2.25 moles) of acetone is added over a period of 15 minutes to the reaction mass with stirring. After addition of the acetone, the reaction mass is heated to 50°-60° C. and maintained at 50°-60° C. for a period of 2.5 hours while being monitored using GLC. The reaction mass is complete at the end of the 2.5 hour period. The reaction mass is then cooled to room temperature and 200 cc of water is added with stirring. The reaction mass is then neutralized with 65 cc of a 50% aqueous acetic acid solution. The organic phase is then separated from the aqueous phase and the organic phase is washed with one 200 cc of portion of water followed by one 200 cc portion of a 10% sodium bicarbonate solution. The resulting product is dried over anhydrous magnesium sulfate, stripped of solvent and distilled on a 12" stone-packed column yielding the following fractions:

| Fraction Number | Vapor Temp. (°C.) | Liquid Temp. (°C.) | Pressure mm/Hg. | Weight of Fraction (grams) |
|---|---|---|---|---|
| 1 | 95/120 | 160/165 | 2.0/2.0 | 5.0 |
| 2 | 140 | 165 | 2.0 | 15.0 |
| 3 | 145 | 180 | 2.0 | 25.0 |
| 4 | 150 | 210 | 2.0 | 24.0 |
| 5 | 150 | 230 | 2.0 | 12.0 |

FIG. 9 is the GLC profile for the crude reaction product containing the compound having the structure:

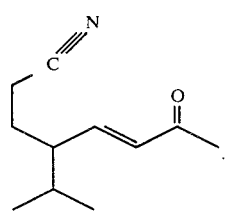

FIG. 10 is the GLC profile for the reaction product immediately prior to distillation (conditions: SE-30 column programmed at 100°-220° C. at 8° C. per minute).

EXAMPLE VII

Preparation of 4-isopropyl-7-oxo-7-octenenitrile

Reaction:

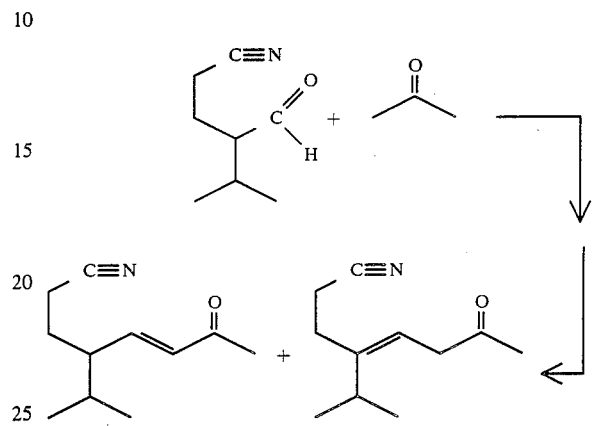

Into a 5-liter reaction flask equipped with stirrer, reflux condenser, addition funnel and thermometer is placed 490 ml of a one-molar solution of sodium hydroxide and 1,250 grams (9.15 moles) of 4-isopropyl-glutaraldehydeonitrile (bulked fractions 4-11 of Example III). 1,062 grams (18.3 moles) of acetone is added over a period of 0.75 hours from the dropping funnel. After addition of the acetone, the reaction mass is heated to 60° C. and the progress of the reaction is monitored using GLC. When the conversion to product is complete; at the end of two hours, a solution of 30 grams of acetic acid in 1,600 ml of saturated sodium chloride is added over a fifteen minute period to the reaction mass. The resulting reaction product has two phases; an organic phase and an aqueous phase. The organic phase is separated from the aqueous phase. The organic phase is washed with one liter of 10% sodium bicarbonate solution. The organic phase is then distilled on a 12" stone saddle-packed column yielding the following fractions:

| Fraction Number | Vapor Temp. (°C.) | Liquid Temp. (°C.) | Pressure mm/Hg. | Weight of Fraction (grams) |
|---|---|---|---|---|
| 1 | 90/110 | 140/160 | 2.0 | 13 |
| 2 | 130 | 165 | 2.0 | 15 |
| 3-8 (bulked) | 145/165 | 165/220 | 2.0 | 464 |

Bulked fractions 3-8 are placed in a two-liter flask. 500 ml toluene and 2.5 grams oxalic acid are then added. The flask is set up with a Bidwell trap and condenser and the contents are refluxed until no additional water collects in the trap. The resulting mixture is cooled to be used in the next reaction.

FIG. 11 is the infra-red spectrum for the compound defined according to the structure:

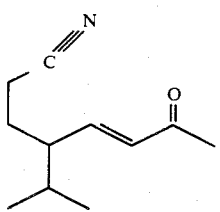

prepared according to this example.

EXAMPLE VIII

Preparation of 8-hydroxy-5-isopropyl-8-methyl-non-6-en-2-one

Reactions:

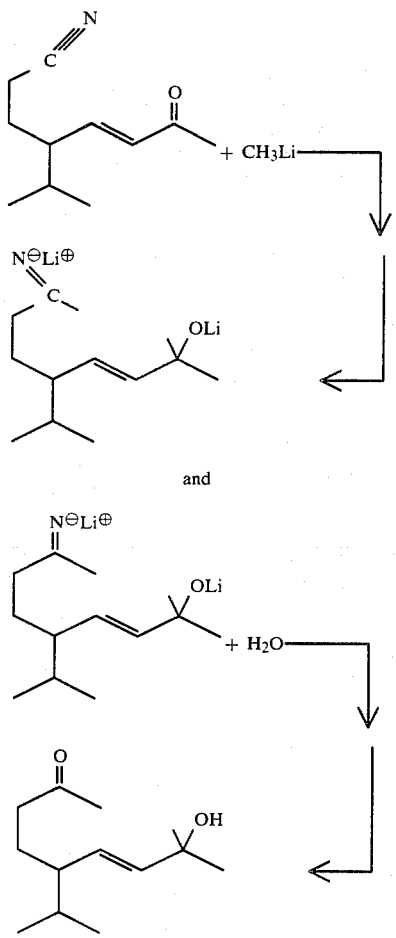

Into a 12-liter reaction vessel equipped with stirrer, thermometer, condenser, gas addition tube (straight, not a dispersion tube), heating mantle and nitrogen blanket apparatus, is placed 4.5 liters of diethylether anhydrous and 120 grams (17.4 moles) of 4–16 mesh lithium shot. The contents of the flask are stirred and refluxed for one hour in order to activate the lithium. The heating mantle is removed and the contents of the flask are allowed to cool to room temperature. 828 grams (8.7 moles) of methyl bromide gas is then added to the reaction mass over a six hour period at a rate such that little gas escapes from the top of the condenser. The reaction is exothermic and will cause the solvent to reflux. When the addition of the methyl bromide is complete and the lithium has dissolved, one liter of toluene is added to the reaction mass. The resulting mixture is cooled to 0°–5° C. and the gas addition tube is replaced by an addition funnel. A toluene solution containing 470 grams of 4-isopropyl-7-oxo-5-octene-nitrile prepared according to Example IV is added dropwise to the reaction mass over a one hour period while maintaining the reaction mass at 0°–5° C. When addition is complete, the reaction mass is allowed to warm to room temperature. A GLC sample at this point shows no starting material and no nitrile present. When the reaction is complete, 800 ml of saturated ammonium chloride solution is added to the reaction mass with stirring. The resulting mixture is stirred for one hour and the organic layer is separated from the aqueous layer. The diethylether solvent is stripped from the reaction mass and the reaction mass is distilled through an 8" stone-packed column yielding the following fractions:

| Fraction Number | Vapor Temp. (°C.) | Liquid Temp. (°C.) | Pressure mm/Hg. | Weight of Fraction (grams) |
|---|---|---|---|---|
| 1 | 120/125 | 150/160 | 0.9 | 38 |
| 2 | 130 | 165 | 0.9 | 72 |
| 3 | 135 | 165 | 0.9 | 102 |
| 4 | 140 | 225 | 1.2 | 72 |

Fractions 2–4 are bulked (246 grams, 45% of theory) and used for the next step in Example IX.

FIG. 12 is the GLC profile for the crude reaction product containing the compound having the structure:

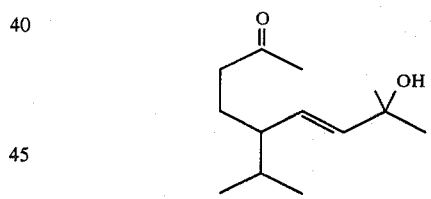

(conditions: SE-30 column programmed at 100°–220° C. at 8° C. per minute).

FIG. 13 is the infra-red spectrum for the compound defined according to the structure:

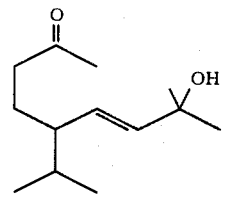

produced according to this example.

EXAMPLE IX

Preparation of solanone

Reaction:

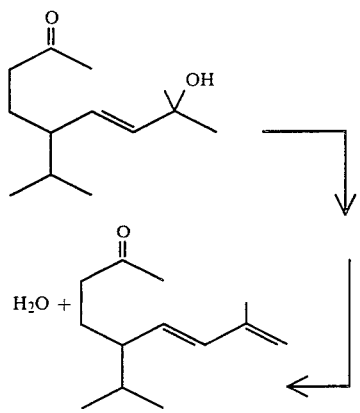

Into a five-liter reaction flask equipped with stirrer, thermometer, condenser, addition funnel, nitrogen blanket apparatus and cooling bath is placed 437 grams (5.5 moles) of pyridine. 720 grams (3.4 moles) of 8-hydroxy-5-isopropyl-8-methyl-non-6-en-2-one produced according to Example VIII (bulked fractions 2–4) is added to the reaction mass in one portion. The resulting mixture is stirred and 229 grams (1.5 moles) of phosphorus oxychloride is added dropwise from the addition funnel over a period of one hour. The reaction is exothermic and the temperature rises to 50° C. where it is controlled by means of a dry ice-isopropyl alcohol bath. After half of the addition of the phosphorous oxychloride, the reaction becomes substantially less exothermic. When addition is complete, the cooling bath is removed and the mixture is stirred for one additional hour during which time a precipitate forms. The mixture is heated to 100° C. to dissolve the precipitate. The source of heating is removed and one liter of water is added dropwise to the reaction mass. The reaction mass is then cooled to room temperature and is now existing in two phases; an aqueous phase and an organic phase.

The aqueous phase is removed from the organic phase and the aqueous phase is extracted twice with 500 ml portions of cyclohexane. The organic layers are combined and extracted with three 300 ml portions of 10% aqueous hydrochloric acid and then washed with two 300 ml portions of water and two 300 ml portions of saturated sodium bicarbonate solution. The solvent is stripped and the product is distilled through a 2" Splash column yielding the following fractions:

| Fraction Number | Vapor Temp. (°C.) | Liquid Temp. (°C.) | Pressure mm/Hg. | Weight of Fraction (grams) |
|---|---|---|---|---|
| 1 | 110–115 | 120 | 1.8 | 16 |
| 2–5 | 115–120 | 140–180 | 1.0 | 350 |
| 6 | 125 | 210 | 1.0 | 120 |

Fractions 2–6 (weighing 470 grams) are redistilled on a 4' Vigreux column (8 plates) yielding the following fractions:

| Fraction Number | Vapor Temp. (°C.) | Liquid Temp. (°C.) | Pressure mm/Hg. | Weight of Fraction (grams) |
|---|---|---|---|---|
| 1 | 45/80 | 90/110 | 0.9 | 11 |
| 2–5 | 82–85 | 110/112 | 0.9 | 83 |
| 6–10 | 85–88 | 112–130 | 0.8 | 331 |

| Fraction Number | Vapor Temp. (°C.) | Liquid Temp. (°C.) | Pressure mm/Hg. | Weight of Fraction (grams) |
|---|---|---|---|---|
| 11 | 100 | 146 | 0.8 | 26 |
| 12 | 110 | 162 | 0.9 | 24 |

Fractions 6–10 are bulked and utilized for their organoleptic properties in creation of a tobacco flavor.

FIG. 14 is the GLC profile for bulked fractions 6–10 of the distillation product above (conditions: Carbowax column programmed at 100°–220° C. at 8° C. per minute). The peak indicated by reference numeral "31" is for the compound having the structure:

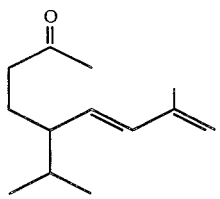

The peak indicated by reference numeral "32" is for the compound having the structure:

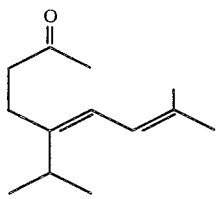

The peak indicated by reference numeral "33" is for the starting material having the structure:

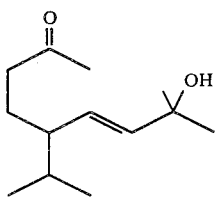

EXAMPLE X

Preparation of ethylene glycol ketal of 4-isopropyl-7-oxo-7-octenenitrile

Reaction:

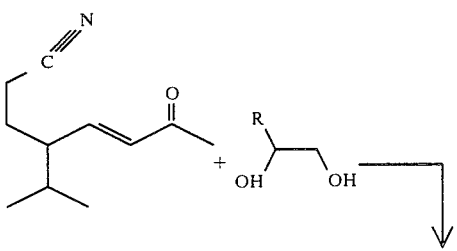

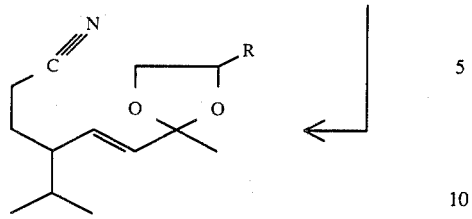

(wherein R represents hydrogen).

Into a one-liter reaction flask equipped with stirrer, reflux condenser, thermometer and heating mantle is placed 239 grams of trimethylorthoformate and 20 grams of Amberlyst ® 15 polystyrene sulfonic acid catalyst manufactured by the Rohm & Haas Company of Philadelphia, Pa. Into the resulting mixture, with stirring, is placed 141 grams of ethylene glycol. The reaction mass is warmed to 25° C. While maintaining the reaction mass at 25° C. with stirring, over a period of 15 minutes, 358 grams of 4-isopropyl-7-oxo-7-octenenitrile (bulked fractions 3–5) is added to the reaction mass. A mild exotherm results. The reaction mass is cooled in order to maintain the temperature at 30°–35° C.

The reaction mass is then aged with stirring for 2.75 hours during which time samples are taken and analyzed using GLC analysis.

When the reaction is complete, the catalyst is separated from the reaction mass using a Buchner funnel and a side-arm flask containing 20 grams of calcium carbonate. The calcium carbonate is filtered and the crude ketal is stripped of solvent using a rotary evaporator. The ketal is then distilled to yield the following fractions:

| Fraction Number | Vapor Temp. (°C.) | Liquid Temp. (°C.) | Pressure mm/Hg. | Weight of Fraction (grams) |
|---|---|---|---|---|
| 1 | 110 | 110 | 2/2 | 22 |
| 2 | 134 | 150 | 2 | 101 |
| 3 | 131 | 151 | 2 | 94 |
| 4 | 134 | 155 | 2 | 106 |
| 5 | 128 | 205 | 2 | 83 |

FIG. 15 is the GLC profile for the crude reaction product. The peak indicated by reference numeral "41" is for the compounds defined according to the structure:

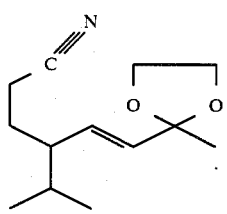

FIG. 16 is the NMR spectrum for the peak indicated by reference numeral "41" of FIG. 15 of this example for the compound having the structure:

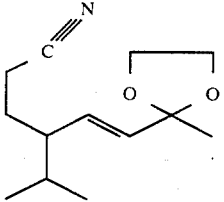

EXAMPLE XI

Preparation of norsolanadione

Reactions:

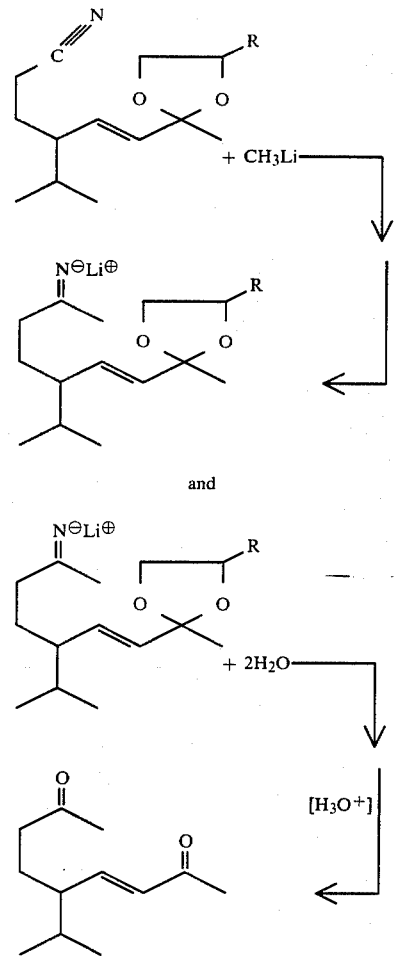

(wherein R represents hydrogen).

Into a 5,000 ml reaction flask equipped with stirrer, thermometer, reflux condenser and heating mantle is placed 66 grams of methyl lithium. The methyl lithium is cooled to 0° C. From an addition funnel, while maintaining the reaction mass at 0°–20° C., bulked fractions 2–5 (557.5 grams) of the ketal reaction product prepared according to Example X is added to the methyl lithium. The addition is carried out over a period of one hour. At the end of the one hour period, the feed of the ketal is complete and the reaction mass is quenched with water followed by 1,000 ml aqueous 10% hydrochloric acid. The reaction mass is then combined with 300 ml concentrated hydrochloric acid causing the pH to drop to 1. The organic phase is separated from the aqueous phase and the organic phase is washed with one liter of 10% sodium carbonate followed by saturated sodium chloride solution. The diethylether is removed on a roto-evaporator.

FIG. 17 is the NMR spectrum for the compound having the structure:

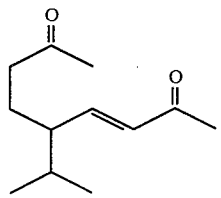

produced according to this example.

EXAMPLE XII

Production of norsolanadione

Reactions:

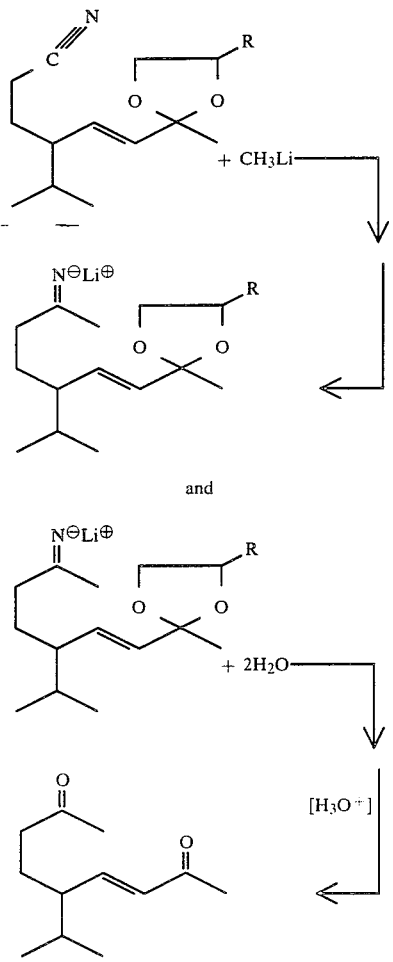

(wherein R represents hydrogen).

Into a 12 liter reaction flask equipped with nitrogen blanket apparatus, stirrer, thermometer and reflux condenser is placed 88 grams (4.0 moles) of methyl lithium dissolved in 400 cc of diethylether. The diethylether solution of methyl lithium is cooled to 0° C. and over a period of 2 hours, 459 grams of the ketal of Example X is added dropwise to the methyl lithium solution while maintaining the reaction temperature at 0°–5° C. When the reaction is complete, the reaction mass is quenched with two liters of a 6 molar aqueous hydrochloric acid solution and the reaction mass is cooled whereby the temperature is maintained at 5°–15° C. The reaction mass is then washed with one 1,000 ml portion of saturated sodium carbonate followed by one 1,000 ml portion of water followed by one 1,000 ml portion of saturated aqueous sodium chloride solution. The organic layer is stripped of solvent using a rotary evaporator and the solvent is distilled yielding the following fractions:

| Fraction Number | Vapor Temp. (°C.) | Liquid Temp. (°C.) | Pressure mm/Hg. | Reflux Ratio | Weight of Fraction (grams) |
|---|---|---|---|---|---|
| 1 | 93/110 | 142/142 | 3.0 | 9:1 | 28 |
| 2 | 122 | 145 | 3.0 | 9:1 | 31 |
| 3 | 125 | 147 | 3.0 | 9:1 | 16 |
| 4 | 125 | 150 | 2.7 | 9:1 | 23 |
| 5 | 122 | 144 | 2.4 | 9:1 | 23 |
| 6 | 123 | 143 | 2.4 | 9:1 | 15 |
| 7 | 122 | 155 | 2.4 | 9:1 | 21 |
| 8 | 125 | 158 | 3.0 | 9:1 | 31 |
| 9 | 125 | 160 | 3.0 | 9:1 | 18 |
| 10 | 124 | 166 | 3.0 | 9:1 | 43 |
| 11 | 125 | 195 | 3.0 | 9:1 | 18 |
| 12 | 120 | 230 | 3.0 | 9:1 | 13 |

FIG. 18 is the infra-red spectrum for the norsolanadione.

FIG. 19 is the mass spectrum for fraction 3 of the foregoing distillation product for norsolanadione.

EXAMPLE XIII

Preparation of 1,2-propylene glycol ketal of 4-isopropyl-7-oxo-7-octenenitrile

Reaction:

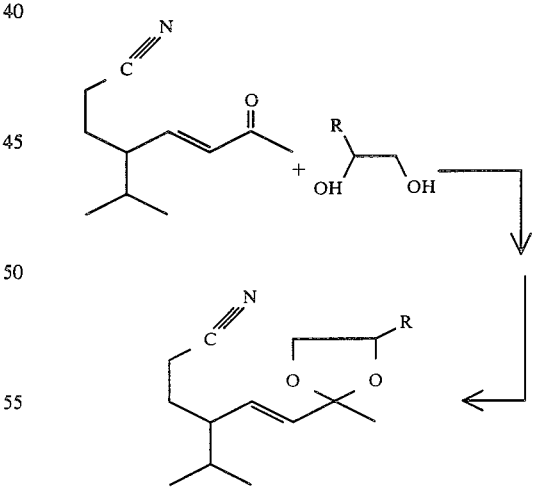

(wherein R represents methyl).

Into a 2,000 ml reaction flask equipped with stirrer, condenser, thermometer and heating mantle is placed 318 grams of trimethylorthoformate and 25 grams of borontrifluoride diethyletherate. While maintaining the reaction mass at a temperature of 5° C. and over a 15 minute period, 228 grams of propylene glycol is added to the resulting mixture with cooling and stirring from the dropping funnel. The reaction mass is then heated to 40° C. and over a two hour period, while maintaining the reaction mass at 40°–50° C., the reaction product of Example VII, bulked fractions 3–8, (4-isopropyl-7-oxo-7-octenenitrile) (537 grams) is added to the reaction mass with stirring. At the end of the addition of the 4-isopropyl-7-oxo-7-octenenitrile, the reaction mass is quenched into 1,000 ml saturated aqueous sodium carbonate solution. The organic phase is separated from the aqueous phase and the organic phase is washed with 10% sodium chloride to neutral (pH=7). The crude reaction mass is then distilled yielding the following fractions:

| Fraction Number | Vapor Temp. (°C.) | Liquid Temp. (°C.) | Pressure mm/Hg. | Weight of Fraction (grams) |
|---|---|---|---|---|
| 1 | 26/25 | 45/70 | 3/3 | 65 |
| 2 | 125 | 150 | 3 | 236 |
| 3 | 120 | 122 | 3 | 217 |
| 4 | 128 | 194 | 3 | 136 |

FIG. 20 is the GLC profile for the crude reaction product.

EXAMPLE XIV

Preparation of 1,2-propylene glycol ketal of 4-isopropyl-7-oxo-7-octenenitrile

Reaction:

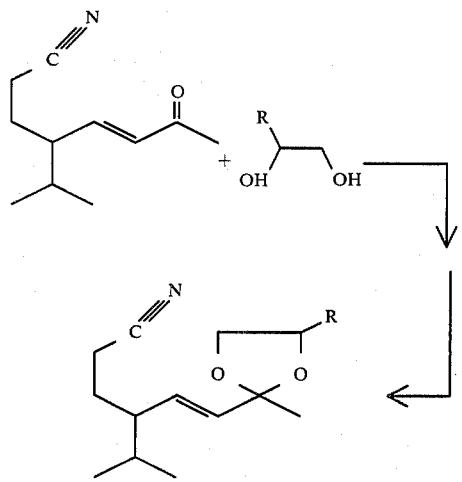

(wherein R represents methyl).

Into a one liter reaction flask equipped with stirrer, thermometer, reflux condenser, heating mantle and cooling bath is placed 130 grams of trimethylorthoformate and 3 drops of concentrated hydrochloric acid. Over a five minute period 92 grams of propylene glycol is slowly added to the reaction mass which exotherms to 5° C. while applying the cooling bath. Over a period of 15 minutes, while maintaining the reaction mass at 14°–16° C., 198 grams of bulked fractions 3–8 of the distillation product of the reaction product of Example VII is added to the reaction mass (a composition of matter consisting primarily of the compound having the structure:

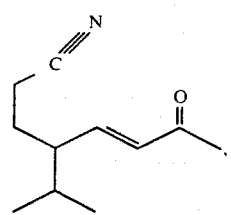

15 drops of concentrated hydrochloric acid is then added to the reaction mass which exotherms to 36° C. The reaction mass is stirred for a period of 1.5 hours at a temperature of 36°–40° C. The reaction mass is then poured into 500 ml of 5% aqueous sodium bicarbonate. The aqueous phase is separated from the organic phase and the organic phase weighs 290 grams. The organic phase is then dried over anhydrous magnesium sulfate and distilled yielding the following fractions:

| Fraction Number | Vapor Temp. (°C.) | Liquid Temp. (°C.) | Pressure mm/Hg. | Weight of Fraction (grams) |
|---|---|---|---|---|
| 1 | 103/122 | 141/150 | 2.6/2 | 50 |
| 2 | 121 | 151 | 1.6 | 50 |
| 3 | 119 | 151 | 1.5 | 50 |
| 4 | 119 | 155 | 1.5 | 50 |
| 5 | 125 | 215 | 1.4 | 85 |

FIG. 21 is the GLC profile for the reaction product of Example XIV.

FIG. 22 is the NMR spectrum for fraction 5 of the foregoing distillation product containing the compound having the structure:

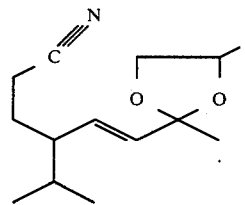

FIG. 23 is the infra-red spectrum for fraction 5 of the foregoing distillation product containing the compound having the structure:

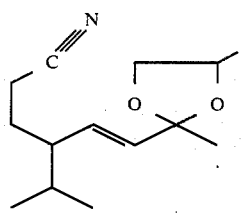

EXAMPLE XV

Preparation of norsolanadione

Reactions:

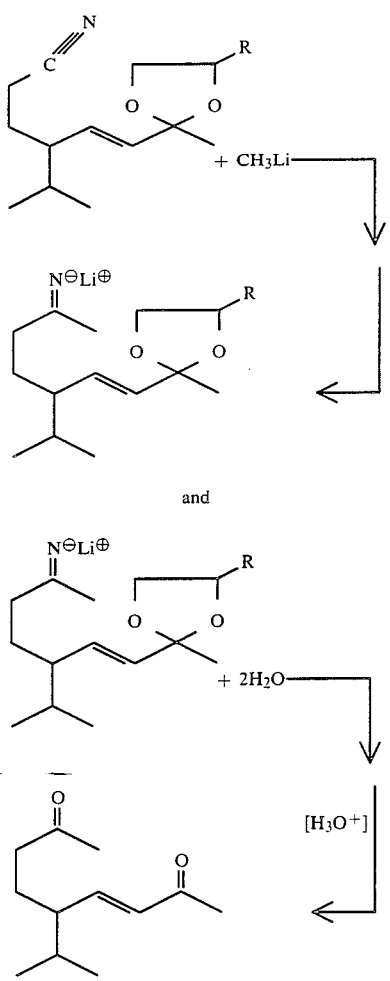

(wherein R represents methyl).

Into a 500 ml reaction flask equipped with nitrogen blanket apparatus, cooling bath, reflux condenser, thermometer and stirrer is placed 110 ml of a 1.6 molar solution of methyl lithium in diethylether. The methyl lithium solution is cooled to 0° C. and over a 30 minute period, the ketal of fraction 5 of the distillation product of Example XIV (35 grams) is added to the reaction mass. The reaction mass is then stirred for a period of 2 hours at 0° C.

The reaction mass is then quenched with 150 ml of a 3M aqueous solution of hydrochloric acid in a 50:50 mixture of methanol and water. 100 ml of saturated aqueous sodium chloride is then added to the reaction mass which is transferred to a separatory funnel. An additional 50 ml of aqueous saturated sodium chloride is added whereupon the layers exist in two phases; an organic phase and an aqueous phase. The organic phase is separated from the aqueous phase and washed with 150 ml of 5% aqueous sodium bicarbonate solution followed by 150 ml of saturated sodium chloride solution. The solvent is stripped on a Rotovap evaporator yielding 19.5 grams of crude reaction product.

The crude reaction product is then distilled yielding norsolanadione at a vapor temperature in the range of 122°–125° C.; a liquid temperature in the range of 144°–158° C.; and a vacuum of 2.4–3.0 mm/Hg.

FIG. 24 is the GLC profile for the crude reaction product prior to distillation (conditions: Carbowax column programmed at 150°–220° C. at 8° C. per minute).

FIG. 25 is the infra-red spectrum for the norsolanadione having the structure:

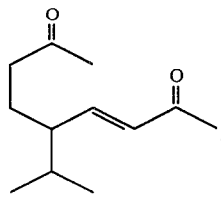

EXAMPLE XVI

Tobacco formulation

A tobacco mixture is produced by admixing the following ingredients:

| Ingredients | Parts by Weight |
| --- | --- |
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |

The following flavor formulation is prepared:

| Ingredients | Parts by Weight |
| --- | --- |
| Ethyl butyrate | 0.05 |
| Ethyl valerate | 0.05 |
| Maltol | 2.00 |
| Cocoa extract | 26.00 |
| Coffee extract | 10.00 |
| Ethyl alcohol | 20.00 |
| Water | 41.90 |

The above stated tobacco flavor formulation is applied at the rate of 1.0% to all cigarettes produced using the above tobacco formulation. Half of the cigarettes are then treated with 500 or 1,000 ppm of the compound defined according to the structure:

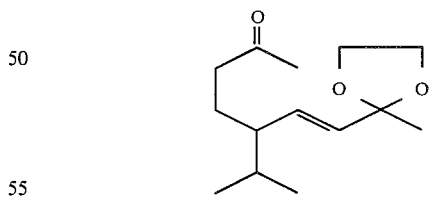

which is a distillation by-product (fraction 12 of the distillation product of the reaction product of Example XII boiling at 120° C. vapor temperature at 3.0 mm/Hg pressure). The control cigarettes not containing said keto ketal produced according to Example XII and the experimental cigarettes which contain the keto ketal of Example XII are evaluated by paired comparison and the results are as follows:

The experimental cigarettes are found to have more body in tobacco smoke flavor and a fuller body sensation. The tobacco-like notes are enhanced and the flavor of the tobacco on smoking is more aromatic with floral, hay, tea-like, sweet and fruity aroma and taste nuances.

The tobacco smoke flavor of the experimental cigarettes, prior to smoking, has floral, sweet and fruity notes. All cigarettes are evaluated for smoke flavor with a 20 mm cellulose acetate filter. The same results are obtained when using the propylene glycol ketal produced as a by-product of Example XV having the structure:

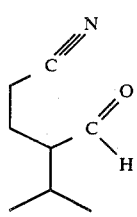

boiling at 120° C. at 2.8 mm/Hg pressure.

What is claimed is:

1. A process for preparing solanone comprising the steps of reacting acetone with an aldehyde having the structure:

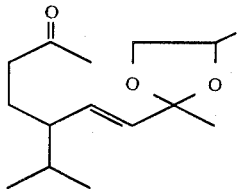

whereby at least one compound defined according to the structure:

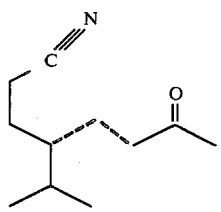

is formed, said reaction being carried out in the presence of base, wherein one of the dashed lines is a carbon-carbon double bond and the other of the dashed lines is a carbon-carbon single bond; reacting at least one compound defined according to the structure:

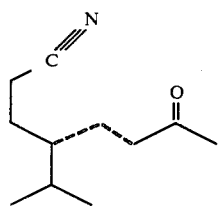

with methyl lithium in order to form at least one compound selected from the group consisting of:

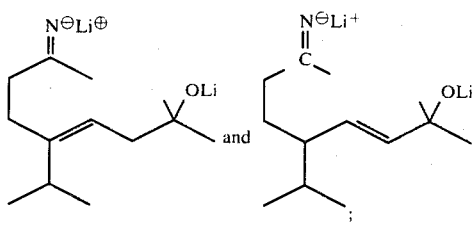

reacting at least one of the compounds having the structures:

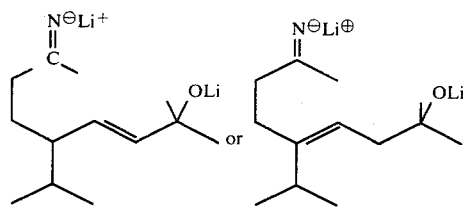

with aqueous acid in order to form at least one compound having a structure selected from the group consisting of:

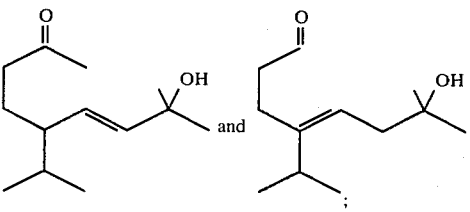

and dehydrating at least one of the compounds having the structure:

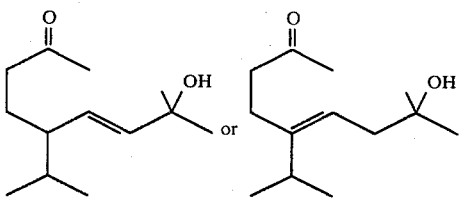

in order to form at least one compound having a structure selected from the group consisting of:

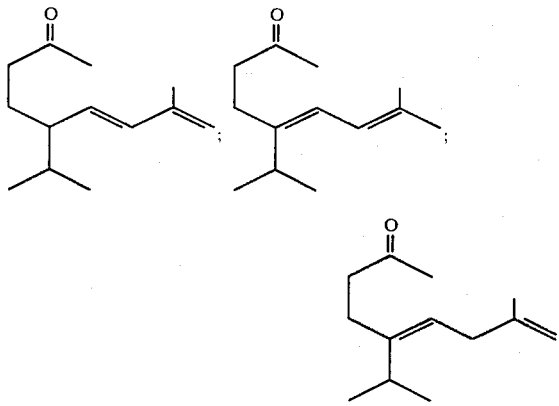

* * * * *